(12) United States Patent
Elbe et al.

(10) Patent No.: US 6,716,881 B2
(45) Date of Patent: Apr. 6, 2004

(54) CARBANILIDES USED AS PESTICIDES

(75) Inventors: Hans-Ludwig Elbe, Wuppertal (DE);
Bernd-Wieland Krüger, Bergisch Gladbach (DE); Robert Markert, Köln (DE); Ralf Tiemann, Leverkusen (DE); Dietmar Kuhnt, Burscheid (DE); Stefan Dutzmann, Langenfeld (DE); Klaus Stenzel, Düsseldorf (DE); Christoph Erdelen, Leichlingen (DE); Martin Kugler, Leichlingen (DE); Hans-Ulrich Buschhaus, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/158,602

(22) Filed: May 30, 2002

(65) Prior Publication Data

US 2003/0078287 A1 Apr. 24, 2003

Related U.S. Application Data

(62) Division of application No. 09/955,783, filed on Sep. 18, 2001, now Pat. No. 6,534,532, which is a division of application No. 09/230,162, filed as application No. PCT/EP97/03694 on Jul. 11, 1997, now Pat. No. 6,319,940.

(30) Foreign Application Priority Data

Jul. 24, 1996 (DE) .......................... 196 29 828

(51) Int. Cl.[7] .................. A01N 37/18; A01N 37/44; A01N 43/56; A01N 43/90
(52) U.S. Cl. .................. 514/617; 514/341; 514/355; 514/374; 514/370; 514/365; 514/432; 514/459; 514/448; 514/599; 514/256; 514/621; 514/622; 514/562; 514/563; 544/319; 546/275.4; 546/316; 548/194; 548/200; 548/233; 548/326; 548/374.1; 549/13; 549/72; 549/425; 562/426; 562/453; 564/74; 564/184; 564/186
(58) Field of Search .................. 564/186, 74, 184; 514/617, 599, 621, 622, 562, 563; 562/426, 453

(56) References Cited

U.S. PATENT DOCUMENTS

| | | | |
|---|---|---|---|
| 3,657,449 A | 4/1972 | Davis et al. | 424/276 |
| 3,674,787 A | 7/1972 | Frey et al. | 260/247 |
| 3,937,840 A * | 2/1976 | Chiyomaru et al. | 424/324 |
| 3,969,510 A * | 7/1976 | Osieka et al. | 424/324 |
| 5,223,526 A | 6/1993 | McLoughlin et al. | 514/406 |
| 5,330,995 A | 7/1994 | Eicken et al. | 514/355 |
| 5,416,103 A | 5/1995 | Eicken et al. | 514/355 |
| 5,438,070 A | 8/1995 | Eicken et al. | 514/403 |
| 5,480,897 A | 1/1996 | Eicken et al. | 514/365 |
| 5,556,988 A | 9/1996 | Eicken et al. | 548/374.1 |
| 5,589,493 A | 12/1996 | Eicken et al. | 514/355 |

FOREIGN PATENT DOCUMENTS

| | | |
|---|---|---|
| DE | 1913178 | 10/1969 |
| EP | 0 371 950 | 1/1995 |
| EP | 0 292 990 | 2/1995 |
| WO | 95/25723 | 9/1995 |

OTHER PUBLICATIONS

J. Org. Chem. (month unavailable), 1994, 59, pp. 5214–5229 XP002044965.
Pestic. Biochem. & Physiol. 25, pp. 188–204 (month unavailable), 1986.
Tetrahedron, vol. 51, No. 41, pp 11165–11176, (month unavailable), 1995—XP002044964.
Chem. Abst., vol. 106, No. 25, Abstract No. 209380.
Chem. Abst., vol. 15, No. 19, Abstract No. 207662.

* cited by examiner

Primary Examiner—Peter O'Sullivan
(74) Attorney, Agent, or Firm—Richard E. L. Henderson; John E. Mrozinski, Jr.

(57) ABSTRACT

The present invention provides carbanilides of formula (I),

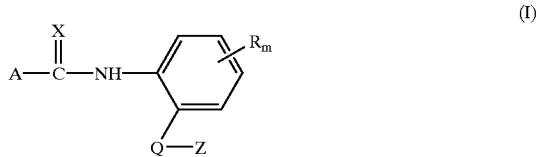

wherein A, Q, R, X, Z and m are as defined herein. A plurality of processes for preparing these compounds is provided, along with methods of using the compounds to control microorganisms in crops and in the protection of materials. The compounds of the present invention also find use in controlling animal pests.

3 Claims, No Drawings

CARBANILIDES USED AS PESTICIDES

This application is a divisional application of U.S. Ser. No. 09/955,783 filed Sep. 18, 2001, now U.S. Pat. No. 6,534,532, which is itself a divisional application of U.S. Ser. No. 09/230,162, filed Jan. 20, 1999, now U.S. Pat. No. 6,319,940, which in turn is a National Stage application under 37 USC §371 of International Application PCT/EP97/03694, filed Jul. 11, 1997.

FIELD OF THE INVENTION

The present invention relates to novel carbanilides, to a plurality of processes for their preparation and to their use for controlling plant and animal pests.

BACKGROUND OF THE INVENTION

It is already known that numerous carboxamides have fungicidal properties (cf. WO 93-11117, EP-A 0 545 099, EP-A 0 589 301 and EP-A 0 589 313). The activity of these compounds is good, but in some cases leaves something to be desired.

DETAILED DESCRIPTION OF THE INVENTION

This invention, accordingly, provides novel carbanilides of the formula

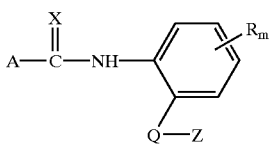
(I)

in which
R represents halogen, nitro, cyano, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkinyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety,
m represents numbers 0, 1, 2, 3 or 4,
A represents a radical of the formula

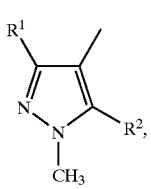

in which
$R^1$ represents halogen, alkyl having 1 to 4 carbon atoms or halogenoalkyl having 1 to 4 carbon atoms and 1 to 5 halogen atoms and
$R^2$ represents hydrogen, halogen, cyano or alkyl having 1 to 4 carbon atoms, or A represents a radical of the formula

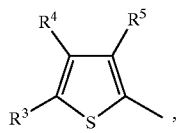

in which
$R^3$ and $R^4$ independently of one another each represent hydrogen, halogen, alkyl having 1 to 4 carbon atoms or halogenoalkyl having 1 to 4 carbon atoms and 1 to 5 halogen atoms and
$R^5$ represents halogen, cyano, alkyl having 1 to 4 carbon atoms or halogenoalkoxy having 1 to 4 carbon atoms and 1 to 5 halogen atoms, or
A represents a radical of the formula

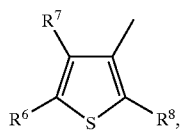

in which
$R^6$ and $R^7$ independently of one another each represent hydrogen, halogen, alkyl having 1 to 4 carbon atoms or halogenoalkyl having 1 to 4 carbon atoms and 1 to 5 halogen atoms and
$R^8$ represents hydrogen, alkyl having 1 to 4 carbon atoms or represents halogen, or
A represents a radical of the formula

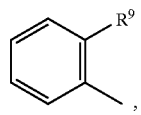

in which
$R^9$ represents halogen, cyano, alkyl having 1 to 6 carbon atoms, halogenoalkyl having 1 to 4 carbon atoms and 1 to 5 halogen atoms, halogenoalkoxy having 1 to 4 carbon atoms and 1 to 5 halogen atoms or represents halogenoalkylthio having 1 to 4 carbon atoms and 1 to 5 halogen atoms, or
A represents a radical of the formula

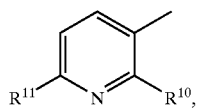

in which
$R^{10}$ represents halogen, cyano, alkyl having 1 to 4 carbon atoms, halogenoalkyl having 1 to 4 carbon atoms and 1 to 5 halogen atoms, alkoxy having 1 to 4 carbon atoms, alkylthio having 1 to 4 carbon atoms or represents halogenoalkoxy having 1 to 4 carbon atoms and 1 to 5 halogen atoms and
$R^{11}$ represents hydrogen, halogen, cyano, alkyl having 1 to 4 carbon atoms, halogenoalkyl having 1 to 4 carbon atoms and 1 to 5 halogen atoms, alkoxy having 1 to 4 carbon atoms, alkylthio having 1 to 4 carbon atoms or represents halogenoalkoxy having 1 to 4 carbon atoms and 1 to 5 halogen atoms, or A represents a radical of the formula

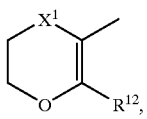

in which
R¹² represents alkyl having 1 to 4 carbon atoms or represents halogenoalkyl having 1 to 4 carbon atoms and 1 to 5 halogen atoms,
X¹ represents a sulphur atom, represents SO, SO₂ or —CH₂, or A represents a radical of the formula

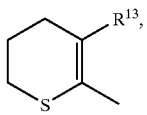

in which
R¹³ represents alkyl having 1 to 4 carbon atoms or represents halogenoalkyl having 1 to 4 carbon atoms and 1 to 5 halogen atoms, or A represents a radical of the formula

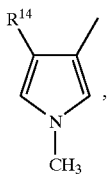

in which
R¹⁴ represents halogen, cyano, alkyl having 1 to 4 carbon atoms or halogenoalkyl having 1 to 4 carbon atoms and 1 to 5 halogen atoms, or A represents a radical of the formula

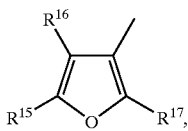

in which
R¹⁵ and R¹⁶ independently of one another each represent hydrogen, halogen, alkyl having 1 to 4 carbon atoms or halogenoalkyl having 1 to 4 carbon atoms and 1 to 5 halogen atoms and
R¹⁷ represents hydrogen, halogen or alkyl having 1 to 4 carbon atoms, or A represents a radical of the formula

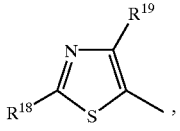

in which
R¹⁸ represents hydrogen, halogen, amino, cyano or alkyl having 1 to 4 carbon atoms and R¹⁹ represents halogen, alkyl having 1 to 4 carbon atoms or halogenoalkyl having 1 to 4 carbon atoms and 1 to 5 halogen atoms, or A represents a radical of the formula

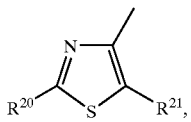

in which
R²⁰ represents hydrogen, halogen, amino, cyano or alkyl having 1 to 4 carbon atoms and
R²¹ represents halogen, alkyl having 1 to 4 carbon atoms or halogenoalkyl having 1 to 4 carbons and 1 to 5 halogen atoms, or A represents a radical of the formula

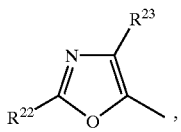

in which
R²² represents hydrogen or alkyl having 1 to 4 carbon atoms and
R²³ represents halogen or alkyl having 1 to 4 carbon atoms, or A represents a radical of the formula

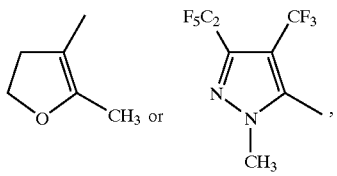

Q represents alkylene having 1 to 4 carbon atoms, alkenylene having 2 to 4 carbon atoms, alkinylene having 2 to 4 carbon atoms or a group of the formula

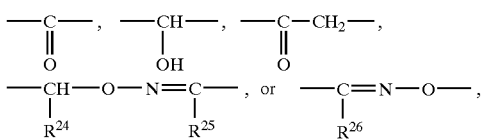

in which
R²⁴, R²⁵ and R²⁶ independently of one another each represent hydrogen, alkyl having 1 to 4 carbon atoms, cycloalkyl having 3 to 6 carbon atoms, alkenyl having 2 to 4 carbon atoms or alkinyl having 2 to 4 carbon atoms, or Q represents a group of the formula

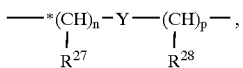

in which
R²⁷ and R²⁸ independently of one another each represent hydrogen or alkyl having 1 to 4 carbon atoms,
Y represents an oxygen atom or represents S(O)ᵣ, where r represents the numbers 0, 1 or 2, and n and p independently of one another each represent the numbers 0, 1 or 2, where the molecular moiety labelled (*) is in each case attached to the phenyl radical of the aniline moiety, X represents oxygen or sulphur and Z represents optionally substituted phenyl, optionally substituted naphthyl, optionally substituted anthracenyl or represents optionally substituted hetaryl.

Furthermore, it has been found that carbanilides of the formula (I) are obtained when a) acyl halides of the formula

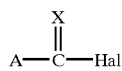

(II)

in which

A and X are each as defined above and

Hal represents halogen are reacted with aniline derivatives of the formula

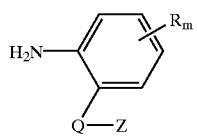

(III)

in which

Q, R, Z and m are each as defined above, if appropriate in the presence of an acid binder and if appropriate in the presence of a diluent, or b) carbanilide derivatives of the formula

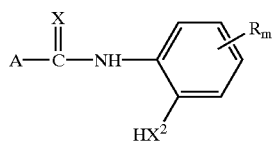

(IV)

in which

A, R, X and m are each as defined above and $X^2$ represents oxygen or sulphur, are reacted with compounds of the formula

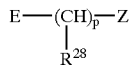

(V)

in which $R^{28}$, Z and p are each as defined above and

E represents a leaving group, if appropriate in the presence of an acid binder and if appropriate in the presence of a diluent, or c) carbanilide derivatives of the formula

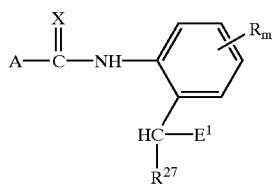

(VI)

in which

A, R, $R^{27}$, X and m are each as defined above and $E^1$ represents a leaving group are reacted with compounds of the formula

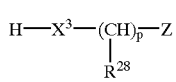

(VII)

in which $R^{28}$, Z and p are each as defined above and $X^3$ represents oxygen or sulphur, if appropriate in the presence of an acid binder and if appropriate in the presence of a diluent, or d) carbanilide derivatives of the formula

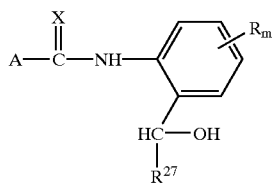

(VIII)

in which

A, R, $R^{27}$, X and m are each as defined above are reacted with compounds of the formula

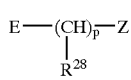

(V)

in which $R^{28}$, Z and p are each as defined above and

E represents a leaving group, if appropriate in the presence of an acid binder and if appropriate in the presence of a diluent or, e) carbanilide derivatives of the formula

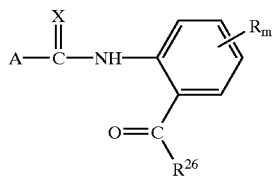

(IX)

in which

A, R, $R^{26}$, X and m are each as defined above are reacted with hydroxylamine derivatives of the formula $$H_2N\text{---}O\text{---}Z \qquad (X)$$

in which
Z is as defined above,
if appropriate in the presence of a catalyst and if appropriate in the presence of a diluent.

Finally, it has been found that the novel carbanilides of the formula (I) are very suitable for use as pesticides. They have microbicidal properties and can be employed for controlling undesirable microorganisms both in crop protection and in the protection of materials. Additionally, they are suitable for controlling animal pests.

Surprisingly, the carbanilides of the formula (I) according to the invention have considerably better fungicidal activity than the constitutionally most similar prior-art carboxamides of the same direction of action.

The formula (I) provides a general definition of the carbanilides according to the invention.

R preferably represents fluorine, chlorine, bromine, nitro, cyano, alkyl having 1 to 6 carbon atoms, halogenoalkyl having 1 or 2 carbon atoms and 1 to 5 fluorine, chlorine and/or bromine atoms, alkoxy having 1 to 6 carbon atoms, halogenoalkoxy having 1 or 2 carbon atoms and 1 to 5 fluorine, chlorine and/or bromine atoms, alkylthio having 1 to 6 carbon atoms, halogenoalkylthio having 1 or 2 carbon atoms and 1 to 5 fluorine, chlorine and/or bromine atoms, alkenyloxy having 2 to 6 carbon atoms, alkinyloxy having 2 to 6 carbon atoms, cycloalkyl having 3 to 7 carbon atoms, carbalkoxy having 1 to 4 carbon atoms in the alkoxy moiety or represents alkoximinoalkyl having 1 to 4 carbon atoms in the alkoxy moiety and 1 to 4 carbon atoms in the alkyl moiety.

m preferably represents the numbers 0, 1, 2 or 3, where R represents identical or different radicals if m represents 2 or 3.

A preferably represents a radical of the formula

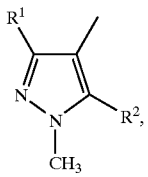

in which
$R^1$ represents fluorine, chlorine, bromine, iodine, methyl, ethyl, isopropyl or halogenoalkyl having 1 or 2 carbon atoms and 1 to 5 fluorine, chlorine and/or bromine atoms and
$R^2$ represents hydrogen, fluorine, chlorine, bromine, iodine, methyl or ethyl.

A furthermore preferably represents a radical of the formula

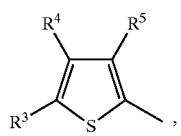

in which
$R^3$ and $R^4$ independently of one another each represent hydrogen, fluorine, chlorine, bromine, methyl, ethyl or halogenoalkyl having 1 or 2 carbon atoms and 1 to 5 fluorine, chlorine and/or bromine atoms and
$R^5$ represents fluorine, chlorine, bromine, cyano, methyl, ethyl or halogenoalkoxy having 1 or 2 carbon atoms and 1 to 5 fluorine, chlorine and/or bromine atoms.

A furthermore preferably represents a radical of the formula

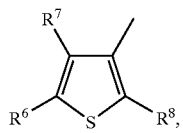

in which
$R^6$ and $R^7$ independently of one another each represent hydrogen, fluorine, chlorine, bromine, methyl, ethyl or halogenoalkyl having 1 to 2 carbon atoms and 1 to 5 fluorine, chlorine and/or bromine atoms and
$R^8$ represents hydrogen, fluorine, chlorine, bromine, methyl or ethyl.

A furthermore preferably represents a radical of the formula

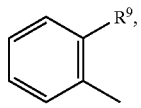

in which
$R^9$ represents fluorine, chlorine, bromine, iodine, cyano, alkyl having 1 to 4 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms or represents halogenoalkylthio having 1 or 2 carbon atoms and 1 to 5 fluorine, chlorine and/or bromine atoms.

A furthermore preferably represents a radical of the formula

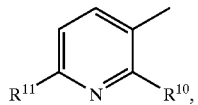

in which
$R^{10}$ represents fluorine, chlorine, bromine, iodine, cyano, methyl, ethyl, halogenoalkyl having 1 or 2 carbon atoms and 1 to 5 fluorine, chlorine and/or bromine atoms, methoxy, ethoxy, methylthio, ethylthio or represents halogenoalkoxy having 1 or 2 carbon atoms and 1 to 5 fluorine, chlorine and/or bromine atoms and
$R^{11}$ represents hydrogen, fluorine, chlorine, bromine, iodine, cyano, methyl, ethyl, halogenoalkyl having 1 or 2 carbon atoms and 1 to 5 fluorine, chlorine and/or bromine atoms, methoxy, ethoxy, methylthio, ethylthio or represents halogenoalkoxy having 1 or 2 carbon atoms and 1 to 5 fluorine, chlorine and/or bromine atoms.

A furthermore preferably represents a radical of formula

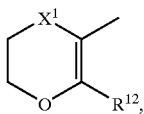

in which
$R^{12}$ represents methyl, ethyl or halogenoalkyl having 1 or 2 carbon atoms and 1 to 5 fluorine, chlorine and/or bromine atoms and
$X^1$ represents a sulphur atom, represents SO, $SO_2$ or —$CH_2$—.

A furthermore preferably represents a radical of formula

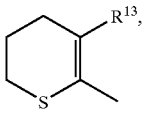

in which
R$^{13}$ represents methyl, ethyl or halogenoalkyl, having 1 or 2 carbon atoms and 1 to 5 fluorine, chlorine and/or bromine atoms.

A furthermore preferably represents a radical of the formula

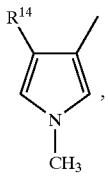

in which
R$^{14}$ represents fluorine, chlorine, bromine, cyano, methyl, ethyl or halogenoalkyl having 1 or 2 carbon atoms and 1 to 5 fluorine, chlorine and/or bromine atoms.

A furthermore preferably represents a radical of the formula

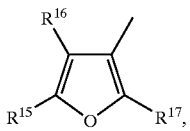

in which
R$^{15}$ and R$^{16}$ independently of one another each represent hydrogen, fluorine, chlorine, bromine, methyl, ethyl or halogenoalkyl having 1 or 2 carbon atoms and 1 to 5 fluorine, chlorine and/or bromine atoms and
R$^{17}$ represents hydrogen, fluorine, chlorine, bromine, methyl or ethyl.

A furthermore preferably represents a radical of the formula

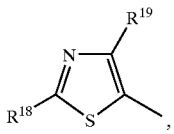

in which
R$^{18}$ represents hydrogen, fluorine, chlorine, bromine, amino, cyano, methyl or ethyl and
R$^{19}$ represents fluorine, chlorine, bromine, methyl, ethyl or halogenoalkyl having 1 or 2 carbon atoms and 1 to 5 fluorine, chlorine and/or bromine atoms.

A furthermore preferably represents a radical of the formula

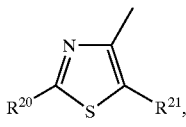

in which
R$^{20}$ represents hydrogen, fluorine, chlorine, bromine, amino, cyano, methyl or ethyl and R$^{21}$ represents fluorine, chlorine, bromine, methyl, ethyl or halogenoalkyl having 1 or 2 carbon atoms and 1 to 5 fluorine, chlorine and/or bromine atoms.

A furthermore preferably represents a radical of the formula

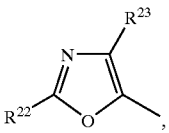

in which
R$^{22}$ represents hydrogen, methyl or ethyl and
R$^{23}$ represents fluorine, chlorine, bromine, methyl or ethyl.

A furthermore preferably represents a radical of the formula

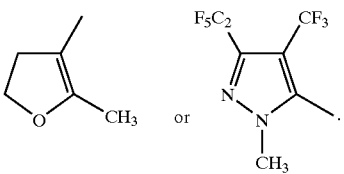

Q preferably represents alkylene having 1 to 3 carbon atoms, alkenylene having 2 or 3 carbon atoms, alkinylene having 2 or 3 carbon atoms or represents a group of the formula

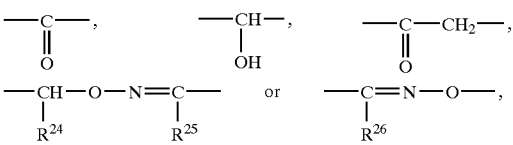

in which
R$^{24}$, R$^{25}$ and R$^{26}$ independently of one another each represent hydrogen, methyl, ethyl, cyclopropyl, cyclopentyl, cyclohexyl, alkenyl having 2 or 3 carbon atoms or alkinyl having 2 or 3 carbon atoms.

Q furthermore preferably represents a group of the formula

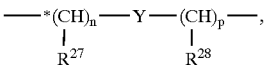

in which
R$^{27}$ and R$^{28}$ independently of one another each represent hydrogen, methyl or ethyl,
Y represents an oxygen atom or represents S(O)$_r$ where r represents the numbers 0, 1 or 2 and
n and p independently of one another each represent the numbers 0, 1 or 2, where the molecular moiety labelled (*) is in each case attached to the phenyl radical of the aniline moiety.

X also preferably represents oxygen or sulphur.

Z preferably represents phenyl, naphthyl or anthracenyl, where each of these radicals may be mono- to trisubstituted by identical or different substituents selected from the group consisting of halogen, alkyl having 1 to 4 carbon atoms, alkylthio having 1 to 4 carbon atoms, halogenoalkyl having 1 to 5 fluorine, chlorine and/or bromine atoms, halogenoalkoxy having 1 or 2 carbon atoms and 1 to 5 fluorine, chlorine and/or bromine atoms, phenyl and phenoxy.

Z furthermore preferably represents hetaryl having 5 or 6 ring members and 1 to 3 heteroatoms, such as oxygen, sulphur and/or nitrogen, where each of the heterocycles may be mono- or disubstituted by identical or different substituents selected from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, phenyl and phenoxy.

R particularly preferably represents fluorine, chlorine, bromine, nitro, cyano, methyl, ethyl, n-propyl, isopropyl, n-butyl, sec-butyl, i-butyl, tert-butyl, trichloromethyl, trifluoromethyl, difluoromethyl, difluorochloromethyl, methoxy, ethoxy, difluoromethoxy, trifluoromethoxy, difluorochloromethylthio, allyloxy, propargyloxy, cyclopropyl, cyclopentyl, cyclohexyl, cycloheptyl, methoxycarbonyl, ethoxycarbonyl, methoximinomethyl, ethoximinomethyl, methoximinoethyl or ethoximinoethyl.

m particularly preferably represents the numbers 0, 1, 2 or 3, where R represents identical or different radicals if m represents 2 or 3.

A particularly preferably represents a radical of the formula

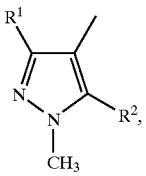

in which $R^1$ represents fluorine, chlorine, bromine, iodine, methyl, ethyl, isopropyl, difluoromethyl, trifluoromethyl, difluorochloromethyl or trichloromethyl and $R^2$ represents hydrogen, fluorine, chlorine, bromine, iodine, methyl or ethyl.

A furthermore particularly preferably represents a radical of the formula

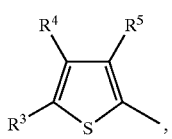

in which $R^3$ and $R^4$ independently of one another each represent hydrogen, fluorine, chlorine, bromine, methyl, ethyl, trifluoromethyl, difluoromethyl, difluorochloromethyl or trichloromethyl and $R^5$ represents fluorine, chlorine, bromine, cyano, methyl, ethyl, trifluoromethoxy, difluoromethoxy, difluorochloromethoxy or trichloromethoxy.

A furthermore particularly preferably represents a radical of the formula

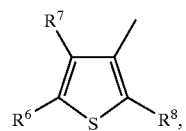

in which $R^6$ and $R^7$ independently of one another each represent hydrogen, fluorine, chlorine, bromine, methyl, ethyl, trifluoromethyl, difluoromethyl, difluorochloromethyl or trichloromethyl and $R^8$ represents hydrogen, fluorine, chlorine, bromine, methyl or ethyl.

A furthermore particularly preferably represents a radical of the formula

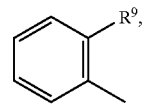

in which $R^9$ represents fluorine, chlorine, bromine, iodine, cyano, methyl, ethyl, n-propyl, isopropyl, n-butyl, i-butyl, sec-butyl, tert-butyl, trifluoromethyl, difluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

A furthermore particularly preferably represents a radical of the formula

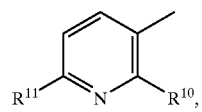

in which $R^{10}$ represents fluorine, chlorine, bromine, iodine, cyano, methyl, ethyl, n-propyl, isopropyl, n-butyl, i-butyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy or trichloromethoxy and $R^{11}$ represents hydrogen, fluorine, chlorine, bromine, iodine, cyano, methyl, ethyl, n-propyl, isopropyl, n-butyl, i-butyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy or trichloromethoxy.

A furthermore particularly preferably represents a radical of the formula

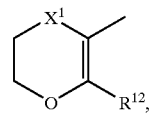

in which $R^{12}$ represents methyl, ethyl, trifluoromethyl, difluoromethyl, difluorochloromethyl or trichloromethyl and $X^1$ represents a sulphur atom, represents SO, SO$_2$ or CH$_2$.

A furthermore particularly preferably represents a radical of the formula

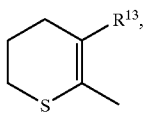

in which

R$^{13}$ represents methyl, ethyl, trifluoromethyl, difluoromethyl, difluorochloromethyl or trichloromethyl.

A furthermore particularly preferably represents a radical of the formula

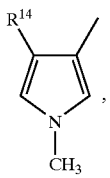

in which

R$^{14}$ represents fluorine, chlorine, bromine, cyano, methyl, ethyl, trifluoromethyl, difluoromethyl, difluorochloromethyl or trichloromethyl.

A furthermore particularly preferably represents a radical of the formula

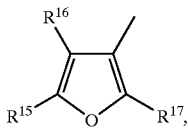

in which

R$^{15}$ and R$^{16}$ independently of one another each represent hydrogen, fluorine, chlorine, bromine, methyl, ethyl, trifluoromethyl, difluoromethyl, difluorochloromethyl or trichloromethyl and R$^{17}$ represents hydrogen, fluorine, chlorine, bromine, methyl or ethyl.

A furthermore particularly preferably represents a radical of the formula

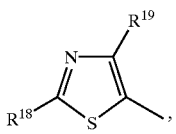

in which

R$^{18}$ represents hydrogen, fluorine, chlorine, bromine, amino, cyano, methyl or ethyl and R$^{19}$ represents fluorine, chlorine, bromine, methyl, ethyl, trifluoromethyl, difluoromethyl, difluorochloromethyl or trichloromethyl.

A furthermore particularly preferably represents a radical of the formula

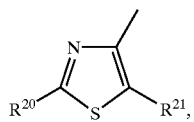

in which

R$^{20}$ represents hydrogen, fluorine, chlorine, bromine, amino, cyano, methyl or ethyl and R$^{21}$ represents fluorine, chlorine, bromine, methyl, ethyl trifluoromethyl, difluoromethyl, difluorochloromethyl or trichloromethyl.

A furthermore particularly preferably represents a radical of the formula

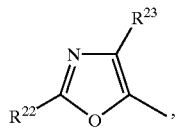

in which

R$^{22}$ represents hydrogen, methyl or ethyl and

R$^{23}$ represents fluorine, chlorine, bromine, methyl or ethyl.

A furthermore particularly preferably represents a radical of the formula

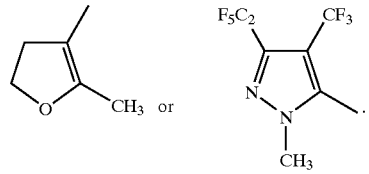

Q particularly preferably represents alkylene having 1 to 3 carbon atoms, alkenylene having 2 or 3 carbon atoms, alkinylene having 2 or 3 carbon atoms or represents a group of the formula

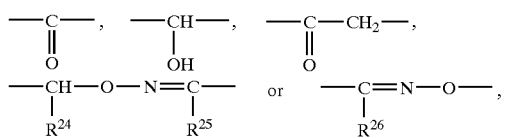

in which

R$^{24}$, R$^{25}$ and R$^{26}$ independently of one another each represent hydrogen, methyl, ethyl, cyclopropyl, cyclopentyl, cyclohexyl, allyl or propargyl.

Q furthermore particularly preferably represents a group of the formula

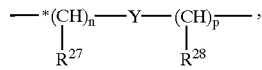

in which

R$^{27}$ and R$^{28}$ independently of one another each represent hydrogen, methyl or ethyl, Y represents an oxygen atom or represents S(O)$_r$, where r represents the numbers 0, 1 or 2, and n and p independently of one another each represent the numbers 0, 1 or 2, where the molecular moiety labelled (*) is in each case attached to the phenyl radical of the aniline moiety.

X also particularly preferably represents oxygen or sulphur.

Z particularly preferably represents phenyl, naphthyl or anthracenyl, where each of these radicals may be mono- to trisubstituted by identical or different substituents selected from the group consisting of fluorine, chlorine, bromine, methyl, ethyl, n-butyl, isopropyl, n-butyl, sec-butyl, i-butyl, tert-butyl, methoxy, ethoxy, methylthio, ethylthio, trifluoromethyl, difluoromethyl, difluorochloromethyl, trichloromethyl, trifluoromethoxy, difluoromethoxy, difluorochloromethoxy, trichloromethoxy, phenyl and phenoxy.

Z furthermore particularly preferably represents pyrrolyl, furyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridyl, pyrimidyl, pyrazinyl or pyridazinyl, where each of these radicals may be mono- or disubstituted by identical or different substituents selected from the group consisting of fluorine, chlorine, bromine, cyano, nitro, methyl, ethyl, n-propyl, isopropyl, n-butyl, sec-butyl, i-butyl, tert-butyl, methoxy, ethoxy, methylthio, ethylthio, trifluoromethyl, difluoromethyl, difluorochloromethyl, trichloromethyl, trifluoromethoxy, difluoromethoxy, difluorochloromethoxy, trichloromethoxy, phenyl and phenoxy.

Using 3-difluoromethoxy-thiophene-2-carbonyl chloride and 2-(2-phenyl-ethen-1-yl)-aniline as starting materials, the course of the process (a) according to the invention can be illustrated by the equation below.

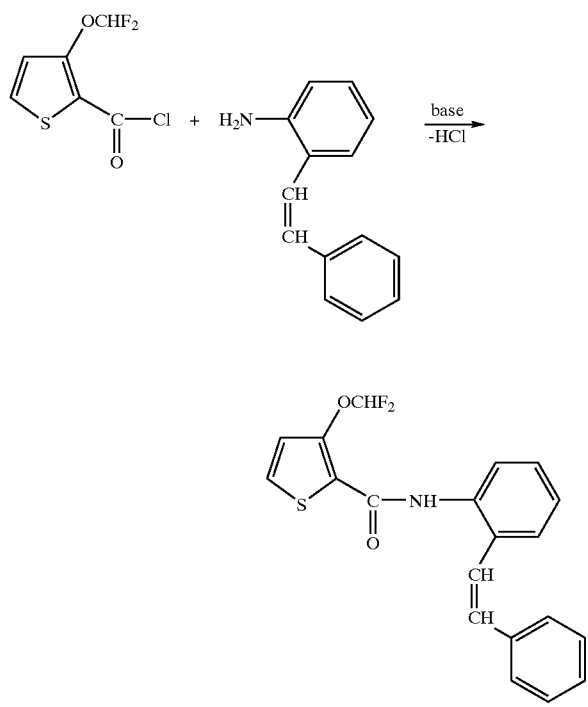

Using 2-hydroxy-11-methyl-3-trifluoromethyl-pyrazole-4-carboxanilide and 2,4-dimethyl-benzylchloride as starting materials, the course of the process (b) according to the invention can be illustrated by the equation below.

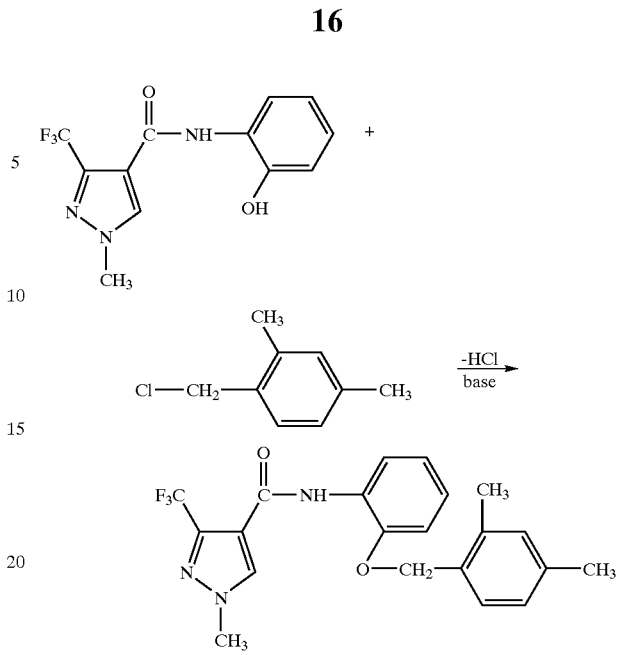

Using 2-bromomethyl-1-methyl-3-trifluoromethyl-pyrazole-4-carboxanilide and 4-chloro-thiophenol as starting materials, the course of the process (c) according to the invention can be illustrated by the equation below.

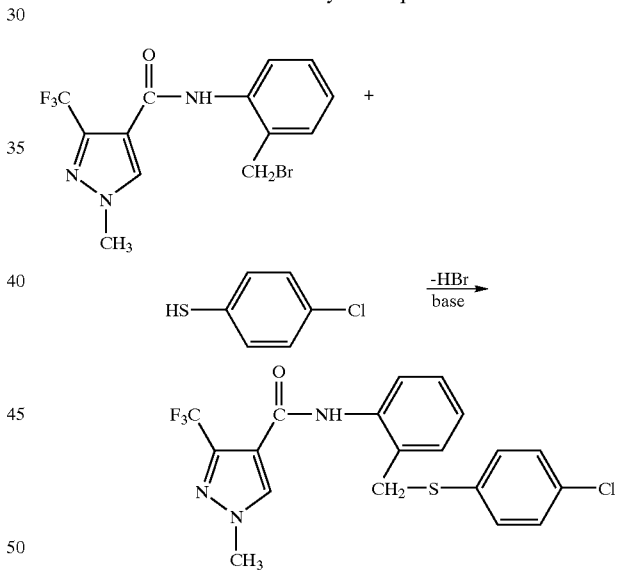

Using 2-hydroxymethyl-1-methyl-3-trifluoromethyl-pyrazole-4-carboxanilide and 2,4-dimethylbenzyl chloride as starting materials, the course of the process (d) according to the invention can be illustrated by the equation below.

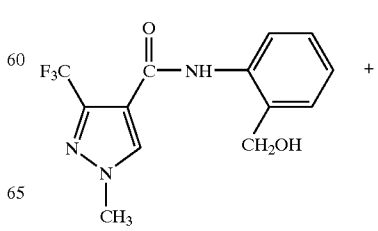

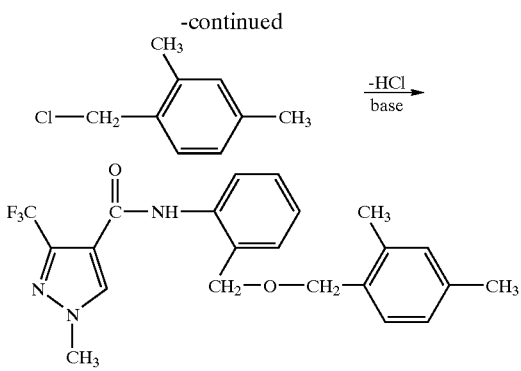

Using 1-methyl-2-methylcarbonyl-3-trifluoromethyl-pyrazole-4-carboxanilide and O-phenyl-hydroxylamine as starting materials, the course of the process (e) according to the invention can be illustrated by the equation below.

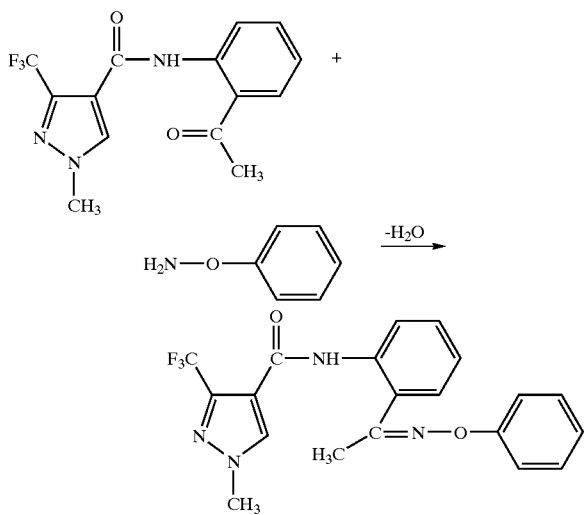

The formula (II) provides a general definition of the acyl halides required as starting materials for carrying out the process (a) according to the invention. In this formula, A and X each preferably have those meanings which have already been mentioned in connection with the description of the compounds of the formula (I) according to the invention as being preferred for these radicals. Hal preferably represents fluorine, chlorine or bromine.

The acyl halides of the formula (II) are known or can be prepared by known methods (cf. WO 93-11117, EP-A 0 545 099, EP-A 0 589 301 and EP-A 0 589 313).

The formula (III) provides a general definition of the aniline derivatives required as reaction components for carrying out the process (a) according to the invention. In this formula Q, R, Z and m each preferably have those meanings which have already been mentioned in connection with the description of the compounds of the formula (I) according to the invention as being preferred for these radicals or this index.

The aniline derivatives of the formula (III) are known or can be prepared by known methods (cf. WO 93-11117, EP-A 0 545 099, EP-A 0 589 301, EP-A 0 371 950 and EP-A 0 292 990).

Suitable acid binders for carrying out the process (a) according to the invention are all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to carry out the reaction without additional acid binder, or to use the amine component in an excess, so that it simultaneously acts as acid binder.

Suitable diluents for carrying out the process (a) according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethylsulphoxide, or sulphones, such as sulpholane.

When carrying out the process (a) according to the invention, the reaction temperatures can be varied within a relatively wide range. In general, the reaction is carried out at temperatures between 0° C. and 120° C., preferably between 10° C. and 100° C.

Both the process (a) according to the invention and the processes (b) to (e) according to the invention are generally carried out under atmospheric pressure. However, it is in each case also possible to carry out the reaction under elevated or reduced pressure.

When carrying out the process (a) according to the invention, generally 1 mol or else an excess of aniline derivative of the formula (III) and 1 to 3 mol of acid binder are employed per mole of acyl halide of the formula (II). However, it is also possible to employ the reaction components in other ratios. Work-up is carried out by customary methods. In general, the reaction mixture is admixed with water, and the organic phase is separated off and, after drying, concentrated under reduced pressure. The residue that remains may, if appropriate, be freed of any impurities that may still be present by customary methods, such as chromatography or recrystallization.

The formula (IV) provides a general definition of the carbanilide derivatives required as starting materials for carrying out the process (b) according to the invention. In this formula A, R, X and m preferably have those meanings which have already been mentioned in connection with the description of the compounds of the formula (I) according to the invention as being preferred for these radicals or this index. $X^2$ also preferably represents oxygen or sulphur.

The carbanilide derivatives of the formula (IV) are known or can be prepared by known methods. Thus, compounds of the formula (IV) are obtained when acyl halides of the formula

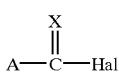

(II)

in which

A, X and Hal are each as defined above
are reacted with amino-phenols or aminothiophenols of the formula

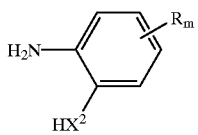

(XI)

in which

R, $X^2$ and m are each as defined above,
if appropriate in the presence of an acid binder, such as, for example, potassium carbonate or a tertiary amine, and if appropriate in the presence of an inert organic diluent, such as, for example, toluene, at temperatures between 20° C. and 150° C.

The amino-phenols or aminothiophenols of the formula (XI) required as reaction components for carrying out the above process are known or can be prepared by known methods.

The formula (V) provides a general definition of the compounds required as reaction components for carrying out the process (b) according to the invention. In this formula, $R^{28}$, Z and p each preferably have those meanings which have already been mentioned in connection with the description of the compounds of the formula (I) according to the invention as being preferred for these radicals or this index. E preferably represents chlorine, bromine, iodine, methylsulphonyloxy, tolylsulphonyloxy or a radical of the formula $R^{29}$—O—$SO_2$—O— or $R^{29}$—O—CO—O—, in which $R^{29}$ represents alkyl having 1 to 4 carbon atoms and preferably represents methyl or ethyl.

The compounds of the formula (V) are also known or can be prepared by known methods.

Suitable acid binders for carrying out the process (b) according to the invention are all inorganic or organic bases which are customary for such reactions. Preference is given to using alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (b) according to the invention are all customary inert organic solvents. Preference is given to using all those diluents which have already been mentioned in connection with the description of the process (a) according to the invention as being preferred.

When carrying out the process (b) according to the invention, the reaction temperatures may also be varied within a relatively wide range. In general, the process is carried out at temperatures between −20° C. and +150° C., preferably between −10° C. and +120° C.

When carrying out the process (b) according to the invention, generally 1 to 2 mol of a compound of the formula (V) and, if appropriate, an equivalent amount or else an excess of acid binder are employed per mole of carbanilide derivative of the formula (IV). Work-up is carried out by customary methods. In general, the reaction mixture is admixed with water and the organic phase is separated off and, after drying, concentrated under reduced pressure. If a water-miscible solvent is employed for carrying out the reaction, the desired product is generally obtained as a solid on dilution of the reaction mixture with water. In this case, the isolation is generally carried out by simple filtering off with suction. The product which is obtained in each case can, if appropriate, be freed of any impurities that may still be present by customary methods, such as chromatography or recrystallization.

The formula (VI) provides a general definition of the carbanilide derivatives required as starting materials for carrying out the process (c) according to the invention. In this formula, A, R, $R^{27}$, X and m each preferably have those meanings which have already been mentioned in connection with the description of the compounds of the formula (I) according to the invention as being preferred for these radicals or this index. $E^1$ preferably represents chlorine, bromine, iodine, methylsulphonyloxy, tolylsulphonyloxy or a radical of the formula $R^{29}$—O—$SO_2$—O— or $R^{29}$—O—CO—O— in which $R^{29}$ represents alkyl having 1 to 4 carbon atoms and preferably represents methyl or ethyl.

The carbanilide derivatives of the formula (VI) are known or can be prepared by known methods.

The formula (VII) provides a general definition of the compounds required as reaction components for carrying out the process (c) according to the invention. In this formula, $R^{28}$, Z and p each preferably have those meanings which have already been mentioned in connection with the description of the compounds of the formula (I) according to the invention as being preferred for these radicals or this index. X3 also preferably represents oxygen or sulphur.

The compounds of the formula (VIII) are also known or can be prepared by known methods.

Suitable acid binders for carrying out the process (c) according to the invention are all inorganic and organic bases which are customary for such reactions. Preference is given to using all those acid acceptors which have already been mentioned in connection with the description of the process (b) according to the invention as being preferred.

Suitable diluents for carrying out the process (c) according to the invention are water and all customary inert, organic solvents. Preference is given using aliphatic, alicyclic or aromatic, optionally halogenated hydrocarbons, such as benzine, benzene, toluene, xylene, chlorobenzene, dichlorobenzene, petroleum ether, hexane, cyclohexane, dichloromethane, chloroform, carbon tetrachloride, ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamides; esters such as methyl acetate or ethyl acetate, sulphoxides, such as dimethyl sulphoxide, alcohols, such as methanol, ethanol, n- or i-propinole, ethylene glycol monomethyl ether, ethylene glycol monoethyl ether, diethylene glycol monomethyl ether, diethylene glycol monoethyl ether, mixtures thereof with water or pure water.

When carrying out the process (c) according to the invention, the reaction temperatures may also be varied within a relatively wide range. In general, the process is carried out at temperatures between −20° C. and +150° C., preferably between −10° C. and +120° C.

When carrying out the process (c) according to the invention, generally 1 to 2 mol of a compound of the formula (VII) and, if appropriate, an equivalent amount or else an excess of acid binder are employed per mole of carbanilide derivative of the formula (VI). Work-up is carried out by customary methods.

The formula (VIII) provides a general definition of the carbanilide derivatives required as starting materials for carrying out the process (d) according to the invention. In this formula, A, R, $R^{27}$, X and m each preferably have those meanings which have already been mentioned in connection with the description of the compounds of the formula (I) according to the invention as being preferred for these radicals or this index.

The carbanilide derivatives of the formula (VIII) are known or can be prepared by known methods.

Suitable acid binders for carrying out the process (d) according to the invention are all inorganic and organic bases which are customary for such reactions. Preference is given to using all those acid acceptors which have already been mentioned as being preferred in connection with the description of the process (b) according to the invention.

Suitable diluents for carrying out the process (d) according to the invention are all customary inert organic solvents. Preference is given to all those diluents which have already been mentioned as being preferred in connection with the description of the process (a) according to the invention.

When carrying out the process (d) according to the invention, the reaction temperatures may also be varied within a relatively wide range. In general, the process is carried out at temperatures between −20° C. and +150° C., preferably between −10° C. and +120° C.

When carrying out the process (d) according to the invention, generally 1 to 2 mol of a compound of the formula (V) and, if appropriate, an equivalent amount or else an excess of acid binder are employed per mole of carbanilide derivative of the formula (VIII). Work-up is carried out by customary methods.

The formula (IX) provides a general definition of the carbanilide derivatives required as starting materials for carrying out the process (e) according to the invention. In this formula, A, R, $R^{26}$, X and m each preferably have those meanings which have already been mentioned in connection with the description of the compounds of the formula (I) according to the invention as being preferred for these radicals or this index.

The carbanilide derivatives of the formula (IX) are known or can be prepared by known methods.

The formula (X) provides a general definition of the hydroxylamine derivatives required as reaction components for carrying out the process according to the invention. In this formula, Z preferably has those meanings which have already been mentioned in connection with the description of the compounds of the formula (I) according to the invention as being preferred for this radical.

The hydroxylamine derivatives of the formula (X) are known or can be prepared by known methods.

Suitable catalysts for carrying out the process (e) according to the invention are all acidic reaction promoters which are customary for such reactions. Preference is given to using hydrogen chloride, sulphuric acid, phosphoric acid, formic acid, acetic acid, trifluoroacetic acid, methane sulphonic acid, trifluoromethanesulphonic acid, toluenesulphonic acid, boron trifluoride (also as etherate), boron tribromide, aluminium trichloride, titanium tetrachloride, tetrabutylorthotitanate, zinc chloride, iron (III) chloride, antimony pentachloride, acidic ion exchangers, acidic alumina and acidic silica gel.

Suitable diluents for carrying out process (e) according to the invention are all inert organic solvents which are customary for such reactions. Preference is given to using aliphatic, alicyclic or aromatic hydrocarbons, such as petroleum ether, hexane, heptane, cyclohexane, methylcyclohexane, benzene, toluene, xylene or decalin; furthermore halogenated hydrocarbons such as chlorobenzene, dichlorobenzene, dichloromethane, chloroform, carbon tetrachloride, dichloroethane or trichloroethane and also nitriles, such as n- or i-butyronitrile or benzonitrile.

When carrying out the process (e) according to the invention, the reaction temperatures can also be varied within a relative wide range. In general, the process is carried out at temperatures between 0° C. and 150° C., preferably between 20° C. and 120° C.

When carrying out the process (e) according to the invention, generally 1 to 2 mol of hydroxylamine derivative of the formula (X) are employed per mole of carbanilide derivative of the formula (IX). Work-up is carried out by customary methods.

The compounds according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae*; and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and fruit and vegetable growing, such as, for example, against Venturia, Podosphaera, Phytophthora and Plasmopara species. They are also very successfully used for controlling rice diseases, such as, for example, Pyricularia species.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The active compounds according to the invention are also suitable for controlling animal pests, in particular insects, arachnids and nematodes, which are encountered in agriculture, in forests, in horticulture in the protection of stored products and of materials, and in the hygiene or veterinary medicine sector, and have good plant tolerance and favourable toxicity to warm-blooded animals. The compounds are active against normally sensitive and resistant species and against pests in all or some stages of development. The abovementioned animal pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia*

*brumata, Lithocolletis blancardella, Hyponomeuta padella, Plutella maculipennis, Malacosoma neustria, Fuproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia Spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes, include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacrylisobutyl, bialaphos, binapacryl, biphenyl, bitertanol, blasticdin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole, imazalil, imibenconazole, iminoctadine, iminoctadine albesilate, iminoctadine triacetate,
iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
2',6'-dibromo-2-methyl-4'-trifluoromethoxy-4'-trifluoromethyl-1,3-thiazole-5-carboxanilide,
2,6-dichloro-N-(4-trifluoromethylbenzyl)-benzamide,
2-aminobutane,
2-phenylphenol (OPP)
8-hydroxyquinoline sulphate,
cis-1-(4-chlorophenyl)-2-(1H-1,2,4-triazol-1-yl)-cycloheptanol,
(5RS,6RS)-6-hydroxy-2,2,7,7-tetramethyl-5-(1H-1,2,4-triazol-1-yl)-3-octanone,
α-(2,4-dichlorophenyl)-p-methoxy-a-methyl-1H-1,2,4-triazole-1-ethanol,
α-(1,1-dimethylethyl)-P-(2-phenoxyethyl)-1H-1,2,4-triazole-1-ethanol,
1-[1-[2-[(2,4-dichlorophenyl)-methoxy]-phenyl]-ethenyl]-1H-imidazole,
bis-(1-methylethyl)-3-methyl-4-[(3-methylbenzoyl)-oxy]-2,5-thiophenedicarboxylate,
2,6-dichloro-N-[[4-(trifluoromethyl)-phenyl]-methyl]-benzamide,
(E)-α-(methoxyimino)-N-methyl-2-phenoxy-phenylacetamide,
9H-xanthene-2-[(phenylamino)-carbonyl]-9-carboxylic hydrazide,
O-methyl S-phenyl phenylpropylphosphoramidothioate,
N-(5-chloro-2-methylphenyl)-2-methoxy-N-(2-oxo-3-oxazolidinyl)-acetamide,
1-(2,4-dichlorophenyl)-2-(1H-1,2,4-triazol-1-yl)-ethanone-O-(phenylmethyl)-oxime,
N-(2,6-dimethylphenyl)-2-methoxy-N-(tetrahydro-2-oxo-3-thienyl)-acetamide,
cis-4-[3-[4-(1,1-dimethylpropyl)-phenyl-2-methylpropyl]-2,6-dimethyl-morpholinehydrochloride,
1-(3,5-dichlorophenyl)-3-(2-propenyl)-2,5-pyrrolidindione,
1-methyl-5-nonyl-2-(phenylmethyl)-3-pyrrolidinole,
1-[[2-(4-chlorophenyl)-3-phenyloxiranyl]-methyl]-1H-1,2,4-triazole,
methanetetrathiol sodium salt
2-(2,3,3-triiodo-2-propenyl)-2H-tetrazole,
N-[3-chloro-4,5-bis(2-propinyloxy)-phenyl]-N'-methoxy-methaneimideamide,
α-(5-methyl-1,3-dioxan-5-yl)-P-[[4-(trifluoromethyl)-phenyl]-methylene]-1H-1,2,4-triazole-1-ethanol,
1-(2-methyl-1-naphthalenyl)-1H-pyrrol-2,5-dione,
N-(2,6-dimethylphenyl)-2-methoxy-N-(tetrahydro-2-oxo-3-thienyl)-acetamide,
3,4-dichloro-1-[4-(difluoromethoxy)-phenyl]-1H-pyrrol-2,5-dione,
N-[2,2,2-trichloro-1-[(chloroacetyl)-amino]-ethyl]-benzamide,
N-formyl-N-hydroxy-DL-alanine-sodium salt,
N-(4-cyclohexylphenyl)-1,4,5,6-tetrahydro-2-pyrimidine-amine,
4-methyl-tetrazolo[1,5-a]quinazolin-5(4H)-one,
2-chloro-N-(2,6-dimethylphenyl)-N-isothiocyanatomethyl)-acetamide,
ethyl [(4-chlorophenyl)-azo]-cyanoacetate,
N-(4-hexylphenyl)-1,4,5,6-tetrahydro-2-pyrimidineamine,
N-(2-chloro-4-nitrophenyl)-4-methyl-3-nitro-benzenesulphonamide,
methyl N-(chloroacetyl)-N-(2,6-dimethylphenyl)-DL-alaninate,
3-[2-(4-chlorophenyl)-5-ethoxy-3-isoxazolidinyl]-pyridine,
2-[(1-methylethyl)sulphonyl]-5-(trichloromethyl)-1,3,4-thiadiazole,
spiro[2H]-1-benzopyrane-2,1'(3'H)-isobenzofuran]-3'-one,
methyl N-(2,6-dimethylphenyl)-N-(5-isoxazolylcarbonyl)-DL-alaninate, potassium hydrogen carbonate,
1-[[2-(2,4-dichlorophenyl)-1,3-dioxolan-2-yl]-methyl]-1H-imidazole,
1-[(diiodomethyl)-sulphonyl]-4-methyl-benzene,
2-bromo-2-(bromomethyl)-pentanedinitrile,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
methyl 1-(2,3-dihydro-2,2-dimethyl-1H-inden-1-yl)-1H-imidazole-5-carboxylate,
2-chloro-N-(2,3-dihydro-1,1,3-trimethyl-1H-inden-4-yl)-3-pyridinecarboxamide,
O,O-diethyl [2-(dipropylamino)-2-oxoethyl]-ethylphosphoramidothioate, α-(2,4-dichlorophenyl)-β-fluoro-p-propyl-1H-1,2,4-triazole-1-ethanol,
3-(1,1-dimethylpropyl-1-oxo-1H-indene-2-carbonitrile,
2,6-dichloro-5-(methylthio)-4-pyrimidinyl-thiocyanate,
S-methyl 1,2,3-benzothiadiazole-7-carbothioate,
N-(6-methoxy)-3-pyridinyl)-cyclopropanecarboxamide,
3,5-dichloro-N-[cyano-[(1-methyl-2-propynyl)-oxy]-methyl]-benzamide,
4-chloro-2-cyano-N,N-dimethyl-5-(4-methylphenyl)-1H-imidazole-1-sulphonamide,
8-(1,1-dimethylethyl)-N-ethyl-N-propyl-1,4-dioxaspiro[4.5]decane-2-methaneamine,
2,2-dichloro-N-[1-(4-chlorophenyl)-ethyl]-1-ethyl-3-methyl-cyclopropanecarboxamide,
N-(2,3-dichloro-4-hydroxyphenyl)-1-methyl-cyclohexanecarboxamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,
*Bacillus thuringiensis*, bendiocarb, benfuracarb, bensultap, betacyluthrin, bifenthrin, BPMC, brofenprox, bromophos A, bufencarb, buprofezin, butocarboxim, butylpyridaben,
cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulphoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, NI 25, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
RH 5992,
salithion, sebufos, silafluofen, sulfotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the activity spectrum of the active compounds which are to be used according to the invention in the protection of materials, or of the compositions, concentrates or quite generally formulations which can be prepared therefrom, can be increased by adding, if appropriate, further compounds having antimicrobial activity, fungicides, bactericides, herbicides, insecticides or other active compounds for widening the activity spectrum or for achieving particular effects, such as, for example, the additional protection against insects. These mixtures may have a wider spectrum of activity than the compounds according to the invention.

Likewise, when used against animal pests the compounds according to the invention may be present in commercial formulations, and in the use forms prepared from these formulations as a mixture with synergists. Synergists are compounds which increase the activity of the active compounds, without it being necessary for the added synergist to be active itself.

The content of active compound of the use forms prepared from the commercial formulations can be varied within wide ranges. The active compound concentration in the use forms can be from 0.0000001 to 95% by weight of active compound, preferably between 0.0001 and 1% by weight.

Application is carried out in a customary manner adapted to the use forms.

The preparation and the use of the compounds according to the invention is illustrated by the examples below.

PREPARATION EXAMPLES

Example 1

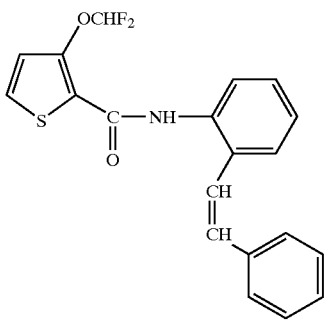
(I-1)

Process (a):

At room temperature, a solution of 0.3 g (0.0015 mol) of 2-(2-phenyl-ethen-1-yl)-aniline in 2 ml of toluene is admixed with a solution of 0.15 g (0.0015 mol) of triethylamine in 10 ml of toluene. At room temperature, 0.33 g (0.0015 mol) of 3-difluoromethoxy-thiophene-2-carbonyl chloride are added to this mixture with stirring. The mixture is subsequently heated to 50° C. and stirred at this temperature for 2 hours. For work-up, the reaction mixture is then cooled to room temperature and admixed with water. The organic phase is separated off, dried over sodium sulphate and then concentrated under reduced pressure at 60° C. The residue that remains is chromatographed over silica gel using diethyl ether. Concentration of the eluate gives 0.53 g (95% of theory) of 2-(2-phenyl-ethen-1-yl)-3-difluoromethoxy-thiophene-2-carboxanilide in the form of a solid substance of melting point 80 to 82° C.

Preparation of Starting Materials:

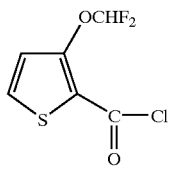

At 80° C., a mixture of 4.2 g (0.022 mol) of 3-difluoromethoxy-thiophene-2-carboxylic acid in 45 ml of toluene is admixed with 3.1 g (0.026 mol) of thionyl chloride. After the addition has ended, the reaction mixture is heated to 90° C. and stirred at this temperature for another 2 hours. The reaction mixture is subsequently concentrated under reduced pressure at 60° C. This gives 4.6 (98.3% of theory) of 3-difluoromethoxy-thiophene-2-carbonyl chloride in the form of an oil.

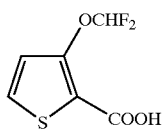

At room temperature, a mixture of 2.4 g of (0.012 mol) of methyl 3-difluoromethoxy-thiophene-2-carboxylate and 5 ml of ethanol is admixed with a solution of 2 g (0.048 mol) of sodium hydroxide in 10 ml of water and then stirred at room temperature for 10 hours. The reaction mixture is then diluted with 50 ml of water and extracted repeatedly with methylene chloride. The aqueous phase is adjusted to a pH of 2 to 3 by addition of dilute hydrochloric acid. The resulting solid product is filtered off with suction, washed with water and dried. This gives 2.2 g (90.15% of theory) of 3-difluoromethoxy-thiophene-2-carboxylic acid in the form of a solid substance of melting point 98 to 100° C.

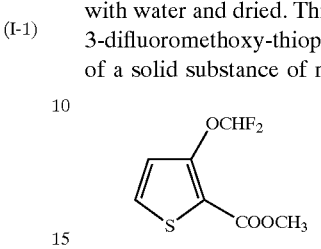

At room temperature, a mixture of 10 g (0.063 mol) of methyl 3-hydroxy-thiophene-2-carboxylate and 90 ml of toluene is admixed with a solution of 5.1 g (0.127 mol) of sodium hydroxide in 8 ml of water. The reaction mixture is heated with stirring to 90° C., 1.1 g of tetrabutylphosphonium bromide are added and 16.4 g (0.189 mol) of chlorodifluoromethane are introduced over a period of 30 minutes. The mixture is then stirred at 90° C. for one hour. The reaction mixture is subsequently cooled to room temperature and admixed with water. The organic phase is separated off, dried over sodium sulphate and then concentrated under reduced pressure at 50° C. The residue that remains is chromatographed over silica gel using cyclohexane:ethyl acetate=3:1 as mobile phase. Concentration of the eluate gives 4.1 g (31.3% of theory) of methyl 3-difluoromethoxy-thiophene-2-carboxylate in the form of an oil.

$^1$H NMR spectrum (CDCl$_3$/TMS): δ=3.833 (s, 3H); 7.463/7.481 (d, 1H) ppm

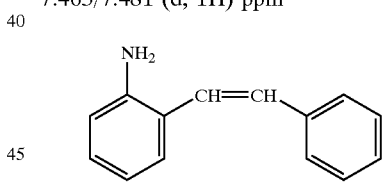

At room temperature, a mixture of 12.9 g (0.057 mol) of 1-phenyl-2-(2-nitro-phenyl)-ethene and 210 ml of 17% strength aqueous hydrochloric acid is admixed with 38.7 g of tin powder and slowly heated to reflux temperature. The mixture is boiled under reflux for 2 hours and then cooled to room temperature and extracted repeatedly with diethyl ether. The organic phase is concentrated under reduced pressure. The residue that remains is admixed with water, and the resulting mixture is neutralized by addition of dilute aqueous sodium hydroxide solution and then extracted repeatedly with methylene chloride. The combined organic phases are dried over sodium sulphate and subsequently concentrated under reduced pressure. The residue that remains is chromatographed over silica gel using cyclohexane:ethyl acetate=3:1. Concentration of the eluate gives 8.5 g (76.4% of theory) of 2-(2-phenylethen-1-yl)-aniline in the form of a solid substance of melting point 80° C.

Example 2

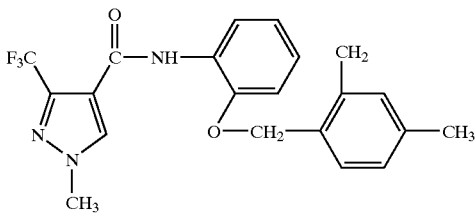

Process (b):

At room temperature, a mixture of 1.0 g (0.0035 mol) of 2-hydroxyphenyl-1-methyl-3-trifluoromethyl-pyrazole-4-carboxanilide, 0.53 g (0.0039 mol) of potassium carbonate and 10 ml of acetonitrile is admixed with stirring with 0.57 g (0.0037 mol) of 2,4-dimethyl-benzyl chloride. After the addition, the reaction mixture is heated to 60° C. and stirred at this temperature for 2 hours. The reaction mixture is subsequently cooled to room temperature and admixed with water. The resulting precipitate is filtered off with suction, washed with water and dried over phosphorus pentoxide at 50° C. under reduced pressure. This gives 1.2 g (85% of the theory) of 2-(2,4-dimethyl-benzyloxy)-1-methyl-3-trifluoromethyl-pyrazole-4-carboxanilide as a solid substance of melting point 123 to 125° C.

Preparation of the Starting Material:

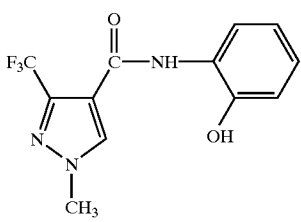

At 100° C., a mixture of 2.4 g (0.022 mol) of 2-aminophenol and 80 ml of toluene is admixed with stirring with a solution of 5.0 g (0.0024 mol) of 1-methyl-3-trifluoromethyl-pyrazole-4-carbonyl chloride in 25 mol of toluene. The reaction mixture is stirred at 100° C. for a further 4 hours and then cooled to room temperature and admixed with water. The resulting precipitate is filtered off with suction and dried under reduced pressure at 50° C. This gives 5.4 g (86.1% of theory) of 2-hydroxyphenyl-1-methyl-3-trifluoromethyl-pyrazole-4-carboxanilide in the form of a solid substance of melting point 191° C.

$^1$H NMR spectrum (d6-DMSO/TMS): δ=3.972 (s, 3H)

Example 3

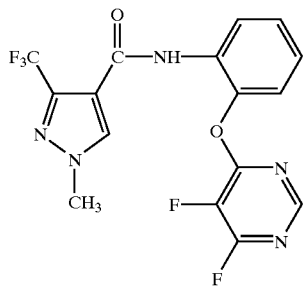

Process (b):

At 15° C., a solution of 3 g (10.5 mol) of 2-hydroxyphenyl-1-methyl-3-trifluoromethyl-pyraxole-4-carboxanilide in 15 ml of dimethylformamide is admixed slowly and with stirring with 0.347 mg of sodium hydride (80% strength in paraffin). This mixture is subsequently added dropwise at 0° C. with stirring to a solution of 1.41 g (10.5 mmol) of 4,5,6-trifluoropyrimidine in 15 ml of dimethylformamide. After the addition has ended, the reaction mixture is stirred for another hour at 0° C. and then concentrated by removal of the solvent under reduced pressure. The residue that remains is admixed with water and stirred vigorously for 2 minutes. The resulting solid product is filtered off with suction, dried and recrystallized from toluene. This gives 3.43 g (81% of theory) of 2-(4,5-difluoro-pyrimdyl-6-oxy)-1-methyl-3-trifluoro-methyl-1-pyrazole-4-carboxanilide in the form of a solid substance of melting point 197° C.

The carbanilides of the formula

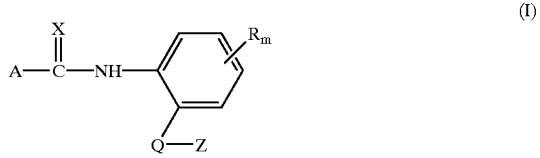

(I)

listed in Table 1 below are also prepared by the methods mentioned above.

TABLE 1

| Ex. No. | A | X | Q | Z | $R_m$ | physic. constant |
|---|---|---|---|---|---|---|
| 4 | ![2-chloro-3-pyridyl] | O | —CH=CH— | ![phenyl] | — | m.p. 154–156° C. |
| 5 | ![2-methyl-4-trifluoromethyl-thiazol-5-yl] | O | —CH=CH— | ![phenyl] | — | m.p. 144–146° C. |

TABLE 1-continued

| Ex. No. | A | X | Q | Z | $R_m$ | physic. constant |
|---|---|---|---|---|---|---|
| 6 | 3-methyl-2-(trifluoromethyl)pyridin-yl | O | —SO₂— | phenyl | — | m.p. 97° C. |
| 7 | 1,3-dimethyl-1H-pyrazol-4-yl | O | —SO₂— | phenyl | — | ¹H NMR** δ = 2.55 (3H) |
| 8 | 2-(trifluoromethyl)phenyl | O | O | phenyl | — | m.p. 68° C. |
| 9 | 1,3-dimethyl-1H-pyrazol-4-yl | O | O | phenyl | — | ¹H NMR** δ = 2.44 (3H) 3.82 (3H) |
| 10 | 2-methyl-4-(trifluoromethyl)-1,3-thiazol-5-yl | O | O | phenyl | — | ¹H NMR** δ = 2.73 (3H) |
| 11 | 2-methyl-4-(trifluoromethyl)-1,3-thiazol-5-yl | O | SO₂ | phenyl | — | m.p. 94° C. |
| 12 | 1-methyl-3-(trifluoromethyl)-1H-pyrazol-4-yl | O | O | phenyl | — | m.p. 95° C. |
| 13 | 1-methyl-3-(trifluoromethyl)-1H-pyrazol-4-yl | O | SO₂ | phenyl | — | m.p. 119° C. |
| 14 | 2,3-dimethylpyridin-yl | O | O | phenyl | — | Oil |
| 15 | 3-bromo-2-methylthien-yl | O | —CH=CH— | phenyl | — | Oil |

TABLE 1-continued

| Ex. No. | A | X | Q | Z | $R_m$ | physic. constant |
|---|---|---|---|---|---|---|
| 16 | 3-CF₃, 4-Me, 1-Me pyrazole | O | —CH=CH— | phenyl | — | m.p. 117° C. |
| 17 | 3-CF₃, 4-Me, 5-Cl, 1-Me pyrazole | O | —CH=CH— | phenyl | — | m.p. 208° C. |
| 18 | 3-Me, 4-Me, 1-Me pyrazole | O | —CH=CH— | phenyl | — | m.p. 123° C. |
| 19 | 3-Me, 2-CF₃ pyridine | O | —CH=CH— | phenyl | — | m.p. 161° C. |
| 20 | 3-CHF₂, 4-Me, 1-Me pyrazole | O | —CH=CH— | phenyl | — | m.p. 122° C. |
| 21 | 3-CHF₂, 4-Me, 1-Me pyrazole | O | O | 4-C(CH₃)₃-phenyl | — | m.p. 110–112° C. |
| 22 | 3-CClF₂, 4-Me, 1-Me pyrazole | O | —CH=CH— | phenyl | — | m.p. 158° C. |
| 23 | 2,3-diMe-1,4-oxathiine | O | —CH=CH— | phenyl | — | ¹H NMR** δ = 2.30 (3H) |
| 24 | 2,3-diMe-1,4-oxathiine-SO₂ | O | —CH=CH— | phenyl | — | ¹H NMR** δ = 2.04 (3H) |
| 25 | 2,3-diMe-1,4-oxathiine-SO | O | —CH=CH— | phenyl | — | ¹H NMR** δ = 2.40 (3H) |

TABLE 1-continued

| Ex. No. | A | X | Q | Z | $R_m$ | physic. constant |
|---|---|---|---|---|---|---|
| 26 | F₃C-pyrazole-CH₃ (N-CH₃) | O | —*O—CH₂— | 2,4-dimethylphenyl | — | m.p. 113–115° C. |
| 27 | F₃C-pyrazole-CH₃ (N-CH₃) | O | —*O—CH₂— | phenyl | — | m.p. 108° C. |
| 28 | F₃C-pyrazole-CH₃ (N-CH₃) | O | —*O—CH₂— | 2-methylphenyl | — | m.p. 123–125° C. |
| 29 | dihydro-oxathiine-CH₃, CF₃ | O | —CH=CH— | phenyl | — | m.p. 177° C. |
| 30 | F₃C-pyrazole-CH₃ (N-CH₃) | O | —*O—CH₂— | 2-chloropyridin-5-yl | — | m.p. 123–126° C. |
| 31 | F₃C-thiazole-CH₃ (2-CH₃) | O | —*O—CH₂— | 2,4-dimethylphenyl | — | m.p. 90–92° C. |
| 32 | F₃C-thiazole-CH₃ (2-CH₃) | O | —*O—CH₂— | 2,4-dimethylphenyl | — | m.p. 83–85° C. |
| 33 | F₃C-thiazole-CH₃ (2-CH₃) | O | —*O—CH₂— | phenyl | — | m.p. 105–107° C. |
| 34 | F₃C-thiazole-CH₃ (2-CH₃) | O | —*O—CH₂— | 2-methylphenyl | — | m.p. 89–91° C. |

TABLE 1-continued

| Ex. No. | A | X | Q | Z | $R_m$ | physic. constant |
|---|---|---|---|---|---|---|
| 35 | 4-CF₃, 2-CH₃-thiazol-5-yl | O | —*O—CH₂— | 2-chloropyridin-5-yl | — | m.p. 158–161° C. |
| 36 | 3-CHF₂, 4-Me, 1-Me-pyrazol-5-yl | O | —*CH₂—S— | phenyl | — | ¹H NMR** δ = 3.88 (3H); 4.12 (2H) |
| 37 | 3-CF₃, 4-Me, 1-Me-pyrazol-5-yl | O | —*CH₂—S— | phenyl | — | m.p. 105° C. |
| 38 | 3-CH₃, 4-Me, 1-Me-pyrazol-5-yl | O | —*CH₂—S— | phenyl | — | m.p. 78° C. |
| 39 | 3-CH₃, 4-Me, 5-Cl, 1-Me-pyrazol | O | —*CH₂—S— | phenyl | — | m.p. 131° C. |
| 40 | 4-CF₃, 2-CH₃-thiazol-5-yl | O | —*CH₂—S— | phenyl | — | m.p. 97° C. |
| 41 | 4-Cl, 2-Cl-thiazol-5-yl | O | —*CH₂—S— | pyridin-3-yl | — | m.p. 99° C. |
| 42 | 3-CH₃, 4-Me, 1-Me-pyrazol-5-yl | O | —*CH₂—S— | 4-CH₃-phenyl | — | m.p. 94° C. |
| 43 | 3-CF₃, 4-Me, 1-Me-pyrazol-5-yl | O | —*CH₂—S— | 4-CH₃-phenyl | — | m.p. 135° C. |

TABLE 1-continued

| Ex. No. | A | X | Q | Z | $R_m$ | physic. constant |
|---|---|---|---|---|---|---|
| 44 | 4-CF₃, 5-methyl, 2-methyl thiazole | O | —*CH₂—S— | 1,4-phenylene-4-CH₃ | — | m.p. 118° C. |
| 45 | 3-CH₃, 4-methyl, 5-Cl, 1-methyl pyrazole | O | —*CH₂—S— | 1,4-phenylene-4-CH₃ | — | m.p. 161° C. |
| 46 | 3-CHF₂, 4-methyl, 1-methyl pyrazole | O | —*CH₂—S— | 1,4-phenylene-4-CH₃ | — | m.p. 108° C. |
| 47 | 3-methyl, 2-Cl pyridine | O | —*O—CH₂— | 2,4-dimethylphenylene | — | m.p. 73–75° C. |
| 48 | 3-methyl, 2-Cl pyridine | O | —*O—CH₂— | 2,5-dimethylphenylene | — | m.p. 98–100° C. |
| 49 | 3-methyl, 2-Cl pyridine | O | —*O—CH₂— | phenyl | — | m.p. 88–90° C. |
| 50 | 3-CHF₂, 4-methyl, 1-methyl pyrazole | O | —*CH₂—O— | 2,4-dimethylphenylene | — | m.p. 120° C. |
| 51 | 3-CH₃, 4-methyl, 1-methyl pyrazole | O | —*CH₂—O— | 2,4-dimethylphenylene | — | m.p. 112° C. |
| 52 | 3-CF₃, 4-methyl, 1-methyl pyrazole | O | —*CH₂—O— | 2,4-dimethylphenylene | — | m.p. 153° C. |

TABLE 1-continued
| Ex. No. | A | X | Q | Z | $R_m$ | physic. constant |
|---|---|---|---|---|---|---|
| 53 | 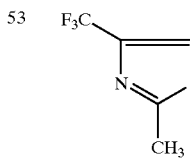 | O | —*CH₂—O— | 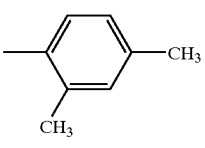 | — | m.p. 167° C. |
| 54 | 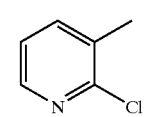 | O | —*CH₂—S— | 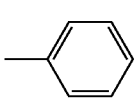 | — | m.p. 108° C. |
| 55 | 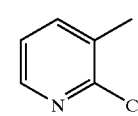 | O | —*CH₂—S— | 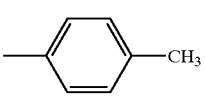 | — | m.p. 131° C. |
| 56 | 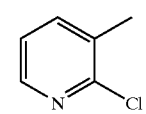 | O | —*O—CH₂— | 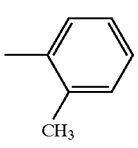 | — | m.p. 104–106° C. |
| 57 | 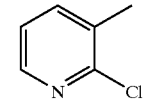 | O | —*O—CH₂— | 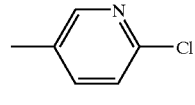 | — | m.p. 130–133° C. |
| 58 | 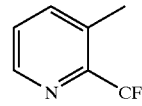 | O | —*CH₂—S— | 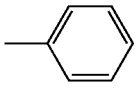 | — | m.p. 133° C. |
| 59 | 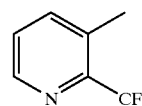 | O | —*CH₂—S— | 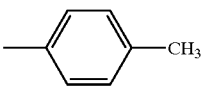 | — | m.p. 133° C. |
| 60 | 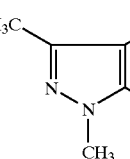 | O | —*CH₂—O— | 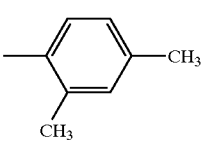 | — | m.p. 153° C. |
| 61 | 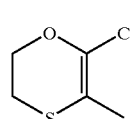 | O | —*CH₂—S— | 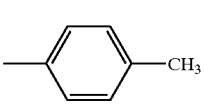 | — | m.p. 112° C. |
| 62 | 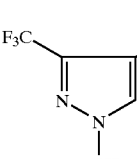 | O | —*O—CH₂— | 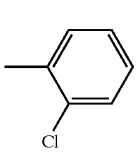 | — | m.p. 129–131° C. |
| 63 | 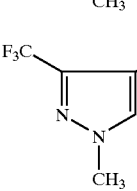 | O | —*O—CH₂— | 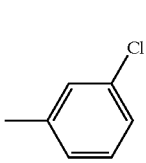 | — | m.p. 137–138° C. |

TABLE 1-continued

| Ex. No. | A | X | Q | Z | $R_m$ | physic. constant |
|---|---|---|---|---|---|---|
| 64 | 3-(trifluoromethyl)-1,4-dimethyl-1H-pyrazol-5-yl | O | —*O—CH$_2$— | 4-chlorophenyl | — | m.p. 128–130° C. |
| 65 | 2,3-dimethyl-5,6-dihydro-1,4-oxathiin-2-yl (2-methyl-3-methyl-1,4-oxathiine) | O | —*CH$_2$—S— | phenyl | — | $^1$H NMR** δ = 2.29 (3H); 4.09 (2H) |
| 66 | 3-(trifluoromethyl)-1,4-dimethyl-1H-pyrazol-5-yl | O | —*O—CH$_2$— | 2-cyanophenyl | — | m.p. 118–120° C. |
| 67 | 3-(trifluoromethyl)-1,4-dimethyl-1H-pyrazol-5-yl | O | —*O—CH$_2$— | 3-cyanophenyl | — | m.p. 158–159° C. |
| 68 | 2-chloro-3-methylpyridin-4-yl | O | —*O—CH$_2$— | 2-chlorophenyl | — | m.p. 98–100° C. |
| 69 | 2-chloro-3-methylpyridin-4-yl | O | —*O—CH$_2$— | 3-chlorophenyl | — | m.p. 112–114° C. |
| 70 | 3-methyl-2-(trifluoromethyl)-5,6-dihydro-1,4-oxathiin (methyl/CF$_3$ 1,4-oxathiine) | O | —*CH$_2$—O— | 2,4-dimethylphenyl | — | m.p. 149° C. |
| 71 | 2,3-dimethyl-5,6-dihydro-1,4-dithiin-2-yl | O | —*O—CH$_2$— | 2,4-dimethylphenyl | — | $^1$H NMR** δ = 2.15 (3H) |
| 72 | 2,3-dimethyl-5,6-dihydro-1,4-oxathiin-2-yl | O | —*O—CH$_2$— | 4-methylphenyl | — | m.p. 118° C. |
| 73 | 2,3-dimethyl-5,6-dihydro-1,4-oxathiin-2-yl | O | —*O—CH$_2$— | 2-chlorophenyl | — | m.p. 122° C. |

TABLE 1-continued
| Ex. No. | A | X | Q | Z | $R_m$ | physic. constant |
|---|---|---|---|---|---|---|
| 74 | 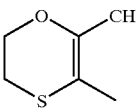 | O | —*O—CH$_2$— | 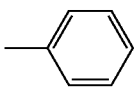 | — | $^1$H NMR** $\delta$ = 2.25 (3H) |
| 75 | 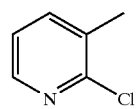 | O | —*O—CH$_2$— | 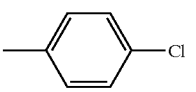 | — | m.p. 110° C. |
| 76 | 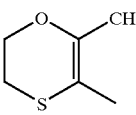 | O | —*O—CH$_2$— | 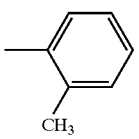 | — | m.p. 76° C. |
| 77 | 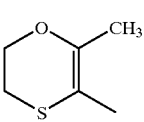 | O | —*O—CH$_2$— | 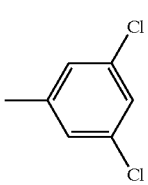 | — | m.p. 135° C. |
| 78 | 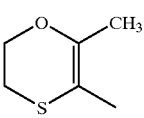 | O | —*O—CH$_2$— | 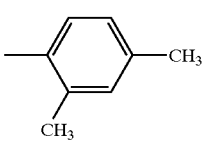 | — | m.p. 94° C. |
| 79 | 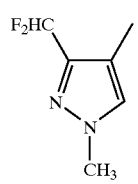 | O | —*CH$_2$—S— | 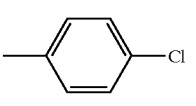 | — | $^1$H-NMR** $\delta$ = 3.89 (3H) 4.08 (2H) |
| 80 | 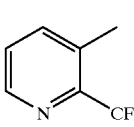 | O | —*CH$_2$—S— | 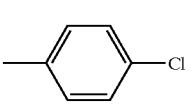 | — | m.p. 169° C. |
| 81 | 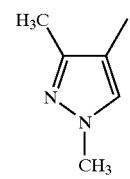 | O | —*CH$_2$—S— | 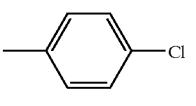 | — | m.p. 119° C. |
| 82 | 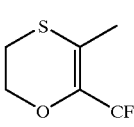 | O | —*CH$_2$—S— | 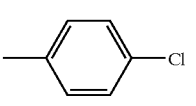 | — | m.p. 155° C. |
| 83 | 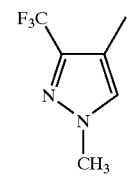 | O | —*CH$_2$—S— | 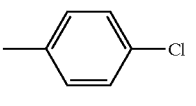 | — | m.p. 115° C. |

TABLE 1-continued
| Ex. No. | A | X | Q | Z | $R_m$ | physic. constant |
|---|---|---|---|---|---|---|
| 84 | 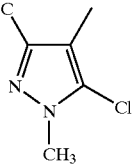 | O | —*CH$_2$—S— | 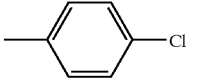 | — | m.p. 97° C. |
| 85 | 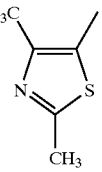 | O | —*CH$_2$—S— | 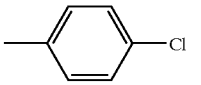 | — | m.p. 112° C. |
| 86 | 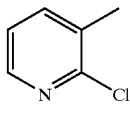 | O | —*O—CH$_2$— | 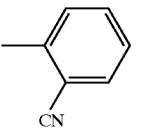 | — | m.p. 140° C. |
| 87 | 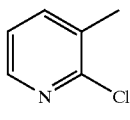 | O | —*O—CH$_2$— | 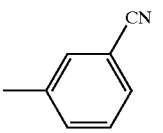 | — | m.p. 115–118° C. |
| 88 | 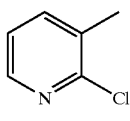 | O | —*O—CH$_2$— | 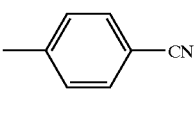 | — | m.p. 165–168° C. |
| 89 | 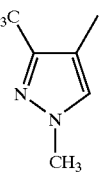 | O | —*O—CH$_2$— | 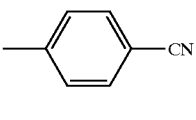 | — | m.p. 182–184° C. |
| 90 | 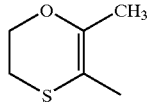 | O | —*CH$_2$—S— | 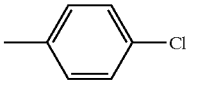 | — | m.p. 116° C. |
| 91 | 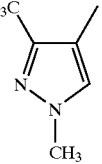 | O | —*CH$_2$—SO— | 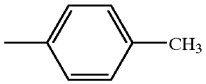 | — | m.p. 182° C. |
| 92 | 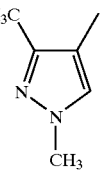 | O | —*CH$_2$—SO— | 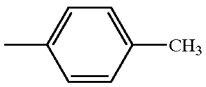 | — | m.p. 165° C. |

TABLE 1-continued

| Ex. No. | A | X | Q | Z | $R_m$ | physic. constant |
|---|---|---|---|---|---|---|
| 93 | F₃C, CH₃ pyrazole, N-CH₃ | O | —*CH₂—SO— | phenyl | — | m.p. 147° C. |
| 94 | H₃C, CH₃ pyrazole, N-CH₃ | O | —*O—CH₂— | 4-CN-phenyl | — | m.p. 137° C. |
| 95 | H₃C, CH₃ pyrazole, N-CH₃ | O | —*O—CH₂— | 2,4-(CH₃)₂-phenyl | — | m.p. 76–78° C. |
| 96 | H₃C, CH₃ pyrazole, N-CH₃ | O | —*O—CH₂— | 2,5-(CH₃)₂-phenyl | — | m.p. 130–132° C. |
| 97 | H₃C, CH₃ pyrazole, N-CH₃ | O | —*O—CH₂— | 2-CH₃-phenyl | — | m.p. 113–115° C. |
| 98 | H₃C, CH₃ pyrazole, N-CH₃ | O | —*O—CH₂— | phenyl | — | m.p. 118° C. |
| 99 | H₃C, CH₃ pyrazole, N-CH₃ | O | —*O—CH₂— | 2-Cl-pyridin-5-yl | — | m.p. 95° C. |
| 100 | H₃C, CH₃ pyrazole, N-CH₃ | O | —*O—CH₂— | 4-Cl-phenyl | — | m.p. 81–82° C. |

TABLE 1-continued

| Ex. No. | A | X | Q | Z | $R_m$ | physic. constant |
|---|---|---|---|---|---|---|
| 101 | 2,3-dimethyl-5,6-dihydro-1,4-oxathiine | O | —*O—CH$_2$— | 3-methylphenyl | — | m.p. 95° C. |
| 102 | 3,4-dimethyl-1-methylpyrazole | O | —*O—CH$_2$— | 3-chlorophenyl | — | m.p. 124° C. |
| 103 | 3,4-dimethyl-1-methylpyrazole | O | —*O—CH$_2$— | 4-chlorophenyl | — | m.p. 149–150° C. |
| 104 | 3,4-dimethyl-1-methylpyrazole | O | —*O—CH$_2$— | 2-cyanophenyl | — | m.p. 60–62° C. |
| 105 | 3-trifluoromethyl-4-methyl-1-methylpyrazole | O | —*CH$_2$—SO$_2$— | 4-methylphenyl | — | m.p. 211° C. |
| 106 | 3,4-dimethyl-1-methylpyrazole | O | —*CH$_2$—SO$_2$— | 4-methylphenyl | — | m.p. 162° C. |
| 107 | 3-trifluoromethyl-4-methyl-1-methylpyrazole | O | —*CH$_2$—SO$_2$— | phenyl | — | $^1$H NMR** δ = 3.93 (3H); 4.36 (2H) |
| 108 | 3,4-dimethyl-1-methylpyrazole | O | —*CH$_2$—SO$_2$— | phenyl | — | m.p. 165° C. |

TABLE 1-continued

| Ex. No. | A | X | Q | Z | $R_m$ | physic. constant |
|---|---|---|---|---|---|---|
| 109 | 3,4-dimethyl-1-methyl-pyrazole | O | —*O—CH$_2$— | 3-cyanophenyl | — | m.p. 166–168° C. |
| 110 | 3,4-dimethyl-1-methyl-pyrazole | O | —*O—CH$_2$— | 4-cyanophenyl | — | m.p. 157–158° C. |
| 111 | 3,4-dimethyl-1-methyl-pyrazole | O | —*O—CH$_2$— | 3-methylphenyl | — | m.p. 92° C. |
| 112 | 3-trifluoromethyl-4-methyl-1-methyl-pyrazole | O | —*O—CH$_2$— | 3-methylphenyl | — | m.p. 108° C. |
| 113 | 2-chloro-3-methyl-pyridine | O | —*O—CH$_2$— | 3-methylphenyl | — | m.p. 118–120° C. |
| 114 | 3-bromo-2-methyl-thiophene | O | O | phenyl | — | $^1$H NMR** $\delta$ = 9.61 (1H, s) |
| 115 | 3,4-dimethyl-1-methyl-pyrazole | O | —*CH$_2$—O— | phenyl | — | $^1$H NMR** $\delta$ = 5.10 (2H, s) |
| 116 | 3-trifluoromethyl-4-methyl-1-methyl-pyrazole | O | —*CH$_2$—O— | phenyl | — | $^1$H NMR** $\delta$ = 5.07 (1H, s) |
| 117 | 2-trifluoromethyl-3-methyl-5,6-dihydro-1,4-oxathiine | O | —*CH$_2$—O— | 4-methylphenyl | — | $^1$H NMR** $\delta$ = 2.29 (3H, s) |

TABLE 1-continued
| Ex. No. | A | X | Q | Z | $R_m$ | physic. constant |
|---|---|---|---|---|---|---|
| 118 | 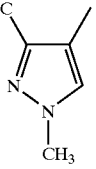 | O | —*CH$_2$—O— | 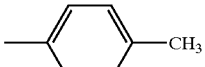 | — | $^1$H NMR** δ = 2.30 (3H) |
| 119 | 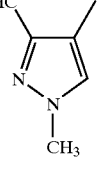 | O | —*CH$_2$—O— | 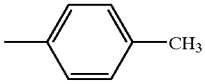 | — | $^1$H NMR** δ = 3.83 (3H) |
| 120 | 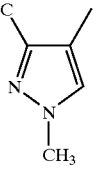 | O | —*CH$_2$—O— | 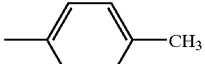 | — | $^1$H NMR** δ = 3.66 (3H) |
| 121 |  | O | —*CH$_2$—O— | 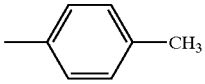 | — | $^1$H NMR** δ = 5.10 (2H) |
| 122 | 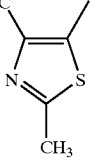 | O | —*CH$_2$—O— | 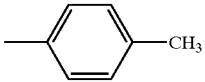 | — | $^1$H NMR** δ = 2.73 (3H) |
| 123 | 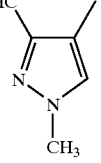 | O | —*CH$_2$—O— | 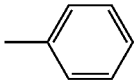 | — | $^1$H NMR** δ = 3.81 (3H) |
| 124 | 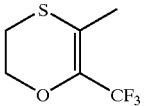 | O | —*CH$_2$—O— | 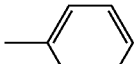 | — | $^1$H NMR** δ = 5.08 (2H) |
| 125 | 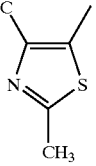 | O | —*CH$_2$—O— | 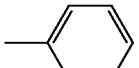 | — | $^1$H NMR** δ = 2.73 (3H) |
| 126 | 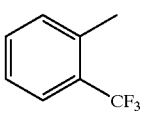 | O | —*CH$_2$—O— | 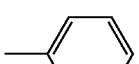 | — | $^1$H NMR** δ = 5.12 (2H) |

TABLE 1-continued
| Ex. No. | A | X | Q | Z | $R_m$ | physic. constant |
|---|---|---|---|---|---|---|
| 127 | 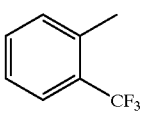 | O | —*CH$_2$—O— | 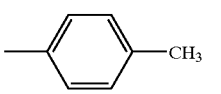 | — | $^1$H NMR** $\delta$ = 2.26 (3H) |
| 128 | 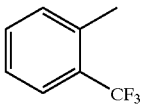 | O | —*CH$_2$—O— | 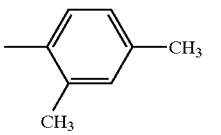 | — | $^1$H NMR** $\delta$ = 1.86 (3H) |
| 129 | 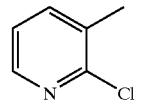 | O | —*CH$_2$—O— | 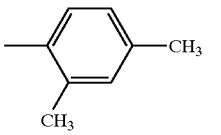 | — | $^1$H NMR** $\delta$ = 2.24 (3H) |
| 130 | 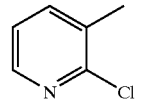 | O | —*CH$_2$—O— | 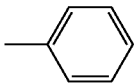 | — | $^1$H NMR** $\delta$ = 5.13 (2H) |
| 131 | 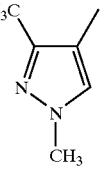 | O | —*CH$_2$—O— | 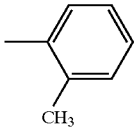 | — | $^1$H NMR** $\delta$ = 3.69 (3H) |
| 132 | 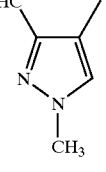 | O | —*CH$_2$—O— | 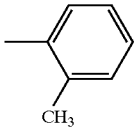 | — | $^1$H NMR** $\delta$ = 3.87 (3H) |
| 133 | 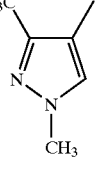 | O | —*CH$_2$—O— | 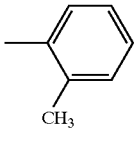 | — | $^1$H NMR** $\delta$ = 3.87 (3H) |
| 134 | 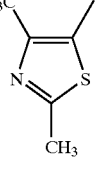 | O | —*CH$_2$—O— | 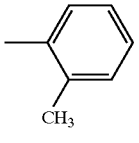 | — | $^1$H NMR** $\delta$ = 2.73 (3H) |
| 135 | 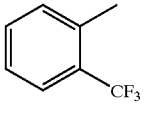 | O | —*CH$_2$—O— | 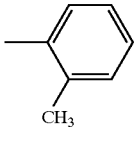 | — | $^1$H NMR** $\delta$ = 5.14 (2H) |

TABLE 1-continued
| Ex. No. | A | X | Q | Z | $R_m$ | physic. constant |
|---|---|---|---|---|---|---|
| 136 | 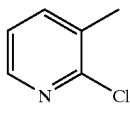 | O | —*CH$_2$—O— | 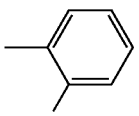 | — | $^1$H NMR** $\delta$ = 2.06 (3H) |
| 137 | 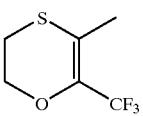 | O | —*CH$_2$—O— | 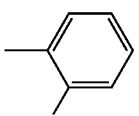 | — | $^1$H NMR** $\delta$ = 5.11 (2H) |
| 138 | 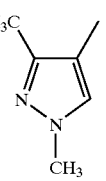 | O | —*CH$_2$—O— | 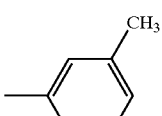 | — | $^1$H NMR** $\delta$ = 3.73 (3H) |
| 139 | 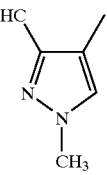 | O | —*CH$_2$—O— | 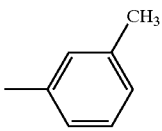 | — | $^1$H NMR** $\delta$ = 3.81 (3H) |
| 140 | 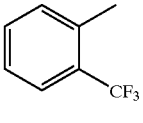 | O | —*CH$_2$—O— | 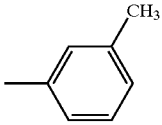 | — | $^1$H NMR** $\delta$ = 5.09 (2H) |
| 141 | 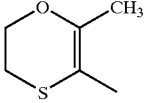 | O | —*CH$_2$—O— | 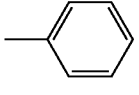 | — | $^1$H NMR** $\delta$ = 2.26 (3H) |
| 142 | 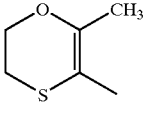 | O | —*CH$_2$—O— | 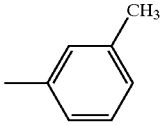 | — | $^1$H NMR** $\delta$ = 5.26 (2H) |
| 143 | 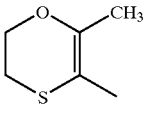 | O | —*CH$_2$—O— | 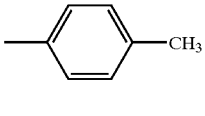 | — | $^1$H NMR** $\delta$ = 2.29 (3H) |
| 144 | 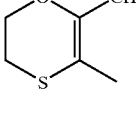 | O | —*CH$_2$—O— | 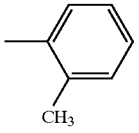 | — | $^1$H NMR** $\delta$ = 5.05 (3H) |
| 145 | 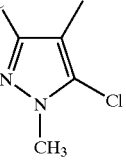 | O | —*CH$_2$—O— | 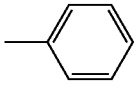 | — | $^1$H NMR** $\delta$ = 3.75 (3H) |

TABLE 1-continued

| Ex. No. | A | X | Q | Z | $R_m$ | physic. constant |
|---|---|---|---|---|---|---|
| 146 | 3,4-dimethyl-5-chloro-1-methylpyrazole | O | —*CH₂—O— | 4-methylphenyl | — | ¹H NMR** δ = 5.04 (2H) |
| 147 | 3,4-dimethyl-5-chloro-1-methylpyrazole | O | —*CH₂—O— | 2-methylphenyl | — | ¹H NMR** δ = 5.07 (3H) |
| 148 | 3,4-dimethyl-5-fluoro-1-methylpyrazole | O | —*CH₂—O— | 2,4-dimethylphenyl | — | m.p. 122° C. |
| 149 | 3,4-dimethyl-5-fluoro-1-methylpyrazole | O | —*CH₂—SO— | 4-methylphenyl | — | m.p. 69° C. |
| 150 | 3,4-dimethyl-5-fluoro-1-methylpyrazole | O | O | phenyl | — | ¹H NMR** δ = 2.39 (3H) |
| 151 | 3,4-dimethyl-5-fluoro-1-methylpyrazole | O | —C(=O)— | phenyl | — | m.p. 166° C. |
| 152 | 3-(OCHF₂)-2-methylthiophene | O | O | phenyl | — | m.p. 112–114° C. |
| 153 | 3,4-dimethyl-5-fluoro-1-methylpyrazole | O | —CH(OH)— | phenyl | — | m.p. 165° C. |
| 154 | 2-(OCHF₂)-methylphenyl | O | O | phenyl | — | m.p. 109–111° C. |

TABLE 1-continued

| Ex. No. | A | X | Q | Z | $R_m$ | physic. constant |
|---|---|---|---|---|---|---|
| 155 | 3-methyl-4-methyl-5-chloro-1-methyl-pyrazole | O | —C(=O)— | phenyl | — | m.p. 95–98° C. |
| 156 | 3-trifluoromethyl-4-methyl-5-chloro-1-methyl-pyrazole | O | —CH(OH)— | phenyl | — | m.p. 133–135° C. |
| 157 | 3-trifluoromethyl-4-methyl-1-methyl-pyrazole | O | —C(=O)— | phenyl | — | m.p. 160° C. |
| 158 | 3-trifluoromethyl-4-methyl-1-methyl-pyrazole | O | —CH(OH)— | phenyl | — | m.p. 178° C. |
| 159 | 3-methyl-2-chloropyridine | O | —C(=O)— | phenyl | — | m.p. 112° C. |
| 160 | 3-methyl-2-chloropyridine | O | —CH(OH)— | phenyl | — | m.p. 133° C. |
| 161 | 3-methyl-4-methyl-1-methyl-pyrazole | O | —C(=O)— | phenyl | — | m.p. 147° C. |
| 162 | 3-methyl-4-methyl-1-methyl-pyrazole | O | —CH(OH)— | phenyl | — | m.p. 63° C. |
| 163 | 3-difluoromethyl-4-methyl-1-methyl-pyrazole | O | —C(=O)— | phenyl | — | m.p. 142° C. |

TABLE 1-continued

| Ex. No. | A | X | Q | Z | $R_m$ | physic. constant |
|---|---|---|---|---|---|---|
| 164 | 3-(F₂HC)-4-methyl-1-methyl-pyrazol-5-yl | O | —CH(OH)— | phenyl | — | m.p. 145–148° C. |
| 165 | 3-(H₃C)-4-methyl-5-F-1-methyl-pyrazol-yl | O | —CH=CH— | phenyl | — | m.p. 133° C. |
| 166 | 2-(OCHF₂)-methyl-phenyl | O | —CH=CH— | phenyl | — | m.p. 70–72° C. |
| 167 | 2-(OCHF₂)-methyl-phenyl | O | —CH(OH)— | phenyl | — | $n_D^{20}$ = 1.5921 |
| 168 | 3-methyl-2-chloro-pyridinyl | O | O | phenyl | — | m.p. 100° C. |
| 169 | 3-(OCHF₂)-2-methyl-thiophen-yl | O | —CH(OH)— | phenyl | — | $n_D^{20}$ = 1.5985 |
| 170 | 3-methyl-2-F-pyridinyl | O | —*CH₂—O— | 2,4-di-CH₃-phenyl | — | m.p. 112° C. |
| 171 | 3-(H₃C)-4-methyl-5-F-1-methyl-pyrazol-yl | O | —*CH₂—O— | 3-Cl-phenyl | — | m.p. 94° C. |
| 172 | 3-(H₃C)-4-methyl-5-F-1-methyl-pyrazol-yl | O | —*CH₂—O— | 2-Cl-phenyl | — | m.p. 109° C. |

TABLE 1-continued
| Ex. No. | A | X | Q | Z | $R_m$ | physic. constant |
|---|---|---|---|---|---|---|
| 173 | 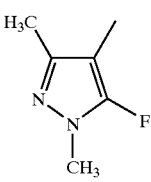 | O | —*CH$_2$—O— | 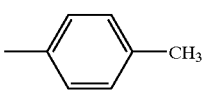 | — | m.p. 79° C. |
| 174 | 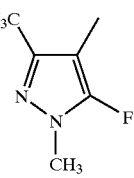 | O | —*CH$_2$—O— | 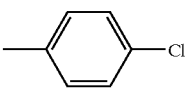 | — | m.p. 99° C. |
| 175 | 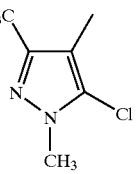 | O | —*CH$_2$—O— | 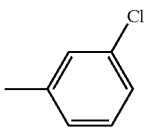 | — | m.p. 110° C. |
| 176 | 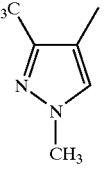 | O | —*CH$_2$—O— | 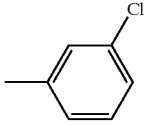 | — | $^1$H NMR** δ = 5.02 (2H) |
| 177 | 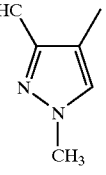 | O | —*CH$_2$—O— | 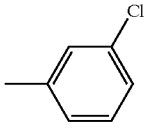 | — | $^1$H NMR** δ = 5.06 (2H) |
| 178 | 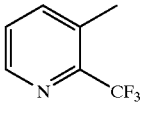 | O | —*CH$_2$—O— | 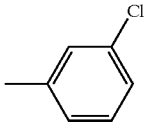 | — | m.p. 120° C. |
| 179 | 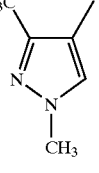 | O | —*CH$_2$—O— | 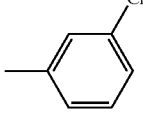 | — | $^1$H NMR** δ = 5.06 (2H) |
| 180 | 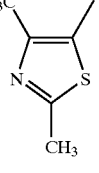 | O | —*CH$_2$—O— | 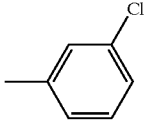 | — | $^1$H NMR** δ = 5.09 (2H) |

TABLE 1-continued

| Ex. No. | A | X | Q | Z | $R_m$ | physic. constant |
|---|---|---|---|---|---|---|
| 181 | 5-chloro-1,3,4-trimethylpyrazole | O | —*CH$_2$—O— | 2-chloro-phenyl | — | m.p. 115° C. |
| 182 | 1,3,4-trimethylpyrazole | O | —*CH$_2$—O— | 2-chloro-phenyl | — | $^1$H NMR** δ = 5.18 (2H) |
| 183 | 1,4-dimethyl-3-trifluoromethylpyrazole | O | —*CH$_2$—O— | 2-chloro-phenyl | — | m.p. 114° C. |
| 184 | 3-difluoromethyl-1,4-dimethylpyrazole | O | —*CH$_2$—O— | 2-chloro-phenyl | — | m.p. 104° C. |
| 185 | 2-trifluoromethylphenyl | O | —*CH$_2$—O— | 2-chloro-phenyl | — | m.p. 137° C. |
| 186 | 2-chloro-3-methylpyridyl | O | —*CH$_2$—O— | 2-chloro-phenyl | — | m.p. 124° C. |
| 187 | 2-methyl-4-trifluoromethylthiazole | O | —*CH$_2$—O— | 2-chloro-phenyl | — | m.p. 103° C. |
| 188 | 3-difluoromethyl-1,4-dimethylpyrazole | O | —*CH$_2$—O— | 4-chloro-phenyl | — | $^1$H NMR** δ = 5.06 (2H) |

TABLE 1-continued
| Ex. No. | A | X | Q | Z | $R_m$ | physic. constant |
|---|---|---|---|---|---|---|
| 189 | 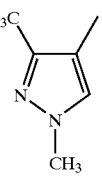 | O | —*CH$_2$—O— | 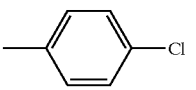 | — | $^1$H NMR** δ = 5.05 (2H) |
| 190 | 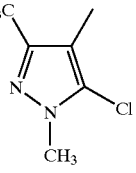 | O | —*CH$_2$—O— | 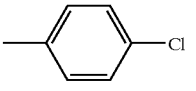 | — | m.p. 143° C. |
| 191 | 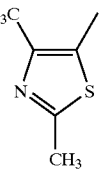 | O | —*CH$_2$—O— | 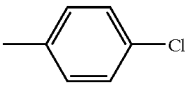 | — | $^1$H NMR** δ = 2.75 (3H) |
| 192 | 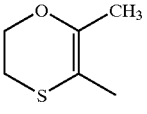 | O | —*CH$_2$—O— | 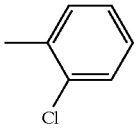 | — | m.p. 99° C. |
| 193 | 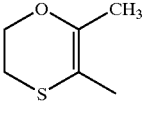 | O | —*CH$_2$—O— | 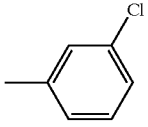 | — | $^1$H NMR** δ = 2.27 (3H) |
| 194 | 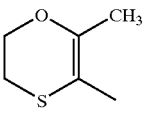 | O | —*CH$_2$—O— | 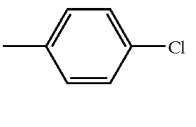 | — | m.p. 116° C. |
| 195 | 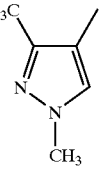 | O | —*CH$_2$—O— | 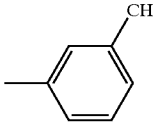 | — | m.p. 88–90° C. |
| 196 | 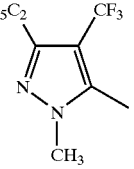 | O | O | 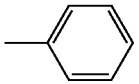 | — | m/e = 479 |
| 197 | 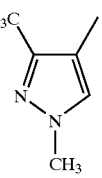 | O | O | 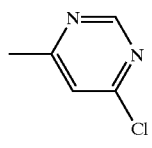 | — | m/e = 397 $\lambda_{max}$ = 262 m$\mu$ |

TABLE 1-continued

| Ex. No. | A | X | Q | Z | $R_m$ | physic. constant |
|---|---|---|---|---|---|---|
| 198 | 3-methyl-2-chloropyridin-yl | O | —*CH₂—O— | 3-CF₃-phenyl | — | m.p. 131° C. |
| 199 | 1,3,4-trimethylpyrazol-5-yl | O | —*CH₂—O—N=C(CH₃)— | 3-CF₃-phenyl | — | m.p. 94° C. |
| 200 | 1,4-dimethyl-3-trifluoromethylpyrazol-5-yl | O | —*CH₂—O—N=C(CH₃)— | 3-CF₃-phenyl | — | m.p. 120° C. |
| 201 | 5-chloro-1,3,4-trimethylpyrazol-5-yl | O | —*CH₂—O—N=C(CH₃)— | 3-CF₃-phenyl | — | m.p. 136° C. |
| 202 | 3-difluoromethyl-1,4-dimethylpyrazol-5-yl | O | —*CH₂—O—N=C(CH₃)— | 3-CF₃-phenyl | — | m.p. 105° C. |
| 203 | 2,3-dimethyl-5,6-dihydro-1,4-oxathiin-yl | O | —*CH₂—O—N=C(CH₃)— | 3-CF₃-phenyl | — | m.p. 76° C. |
| 204 | 5-fluoro-1,3,4-trimethylpyrazol-5-yl | O | —*CH₂—O—N=C(CH₃)— | 3-CF₃-phenyl | — | m.p. 97° C. |
| 205 | 2,3-dimethyl-5,6-dihydro-1,4-oxathiin-yl | O | —*CH₂—O— | 2,4-dimethylphenyl | — | m/e = 369 $\lambda_{max}$ = 293 m$\mu$ |
| 206 | 2,3-dimethylfuran-yl | O | O | phenyl | — | ¹H NMR** δ = 2.60 (3H) |

TABLE 1-continued

| Ex. No. | A | X | Q | Z | $R_m$ | physic. constant |
|---|---|---|---|---|---|---|
| 207 | 3-methyl-2-methyl-4,5-dihydrofuran | O | O | phenyl | — | m.p. 104° C. |
| 208 | 3-methyl-2-methyl-4,5-dihydrofuran | O | —CH=CH— | phenyl | — | m.p. 123° C. |
| 209 | 3-methyl-2-methyl-4,5-dihydrofuran | O | —*CH$_2$—O— | 2-chlorophenyl | — | $^1$H NMR** δ = 5.12 (2H) |
| 210 | 3-methyl-2-methyl-4,5-dihydrofuran | O | —CH(OH)— | phenyl | — | m.p. 143° C. |
| 211 | 3-methyl-2-methyl-4,5-dihydrofuran | O | —*CH$_2$—O— | 4-methylphenyl | — | $^1$H NMR** δ = 2.30 (3H) |
| 212 | 3-methyl-2-methyl-4,5-dihydrofuran | O | —*CH$_2$—O— | 4-chlorophenyl | — | m.p. 111° C. |
| 213 | 3-(chlorodifluoromethyl)-4-methyl-1-methyl-pyrazole | O | O | phenyl | — | m.p. 99° C. |
| 214 | 3-methyl-2-methyl-5,6-dihydro-1,4-oxathiine | O | O | phenyl | — | m.p. 75° C. |
| 215 | 3-methyl-4-methyl-5-chloro-1-methyl-pyrazole | O | O | phenyl | — | m.p. 95° C. |

*The molecular moiety labelled (*) is in each case attached to the phenyl radical of the aniline moiety.
**The $^1$H NMR spectra were recorded in deuterochloroform (CDCl$_3$) using tetramethyl silane (TMS) as internal standard. The chemical shift as δ value in ppm is given.

USE EXAMPLES

Example A
Podosphaera Test (Apple)/Protective

| Solvent: | 47 parts by weight of acetone |
| --- | --- |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray-coating has dried on, the plants are inoculated by dusting with conidia of the causative organism of apple mildew *Podosphaera leucotricha*.

The plants are then placed in a greenhouse at 23° C. and a relative atmospheric humidity of approximately 70%.

Evaluation is carried out 10 days after the inoculation. 0% means an efficacy which corresponds to that of the untreated control, while an efficacy of 100% means that no infection is observed.

Active compounds, active compound concentrations and test results are shown in the table below.

TABLE A

Podosphaera test (apple)/protective

| Active compound | Efficacy in % at an active compound concentration in the spray liquor of 100 ppm |
| --- | --- |
| According to the invention: | |
| 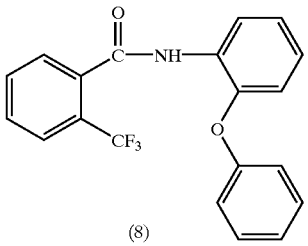 (8) | 100 |
| 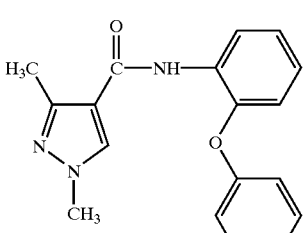 (9) | 96 |

Example B
Venturia Test (Apple)/Protective

| Solvent: | 47 parts by weight of acetone |
| --- | --- |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray-coating has dried on, the plants are inoculated with an aqueous conidia suspension of the causative organism of apple scab *Venturia inaequalis* and then remain in an incubation cabin at 20° C. and 100% relative atmospheric humidity for 1 day.

The plants are then placed in a greenhouse at 23° C. and a relative atmospheric humidity of approximately 70%.

Evaluation is carried out 12 days after the inoculation. 0% means an efficacy which corresponds to that of the untreated control, while an efficacy of 100% means that no infection is observed.

Active compounds, active compound concentrations and test results are shown in the table below.

TABLE B

Venturia test (apple)/protective

| Active compound | Efficacy in % at an active compound concentration in the spray liquor of 100 ppm |
| --- | --- |
| According to the invention: | |
| 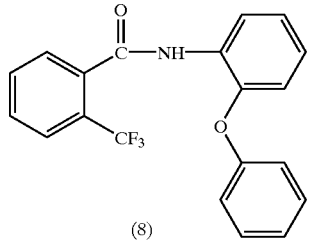 (8) | 83 |
| 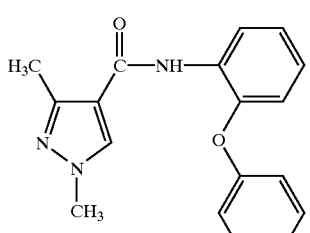 (9) | 83 |
| 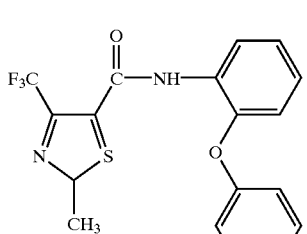 (10) | 94 |
| 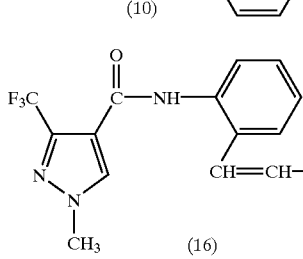 (16) | 97 |

TABLE B-continued

Venturia test (apple)/protective

| Active compound | Efficacy in % at an active compound concentration in the spray liquor of 100 ppm |
|---|---|
| F₂HC–[pyrazole, N-CH₃]–C(O)–NH–[phenyl]–CH=CH–[phenyl]  (20) | 100 |
| F₂HC–[pyrazole, N-CH₃]–C(O)–NH–[phenyl]–CH₂–S–[phenyl]–CH₃  (46) | 100 |
| F₂HC–[pyrazole, N-CH₃]–C(O)–NH–[phenyl]–CH₂–O–[phenyl(CH₃)]–CH₃  (50) | 95 |
| F₃C–[pyrazole, N-CH₃]–C(O)–NH–[phenyl(CH₃)]–CH₂–O–[phenyl-CH₃]  (195) | 90 |

Example C
*Pyrenophora teres* Test (Barley)/Protective

| Solvent: | 10 parts by weight of N-methyl-pyrrolidone |
|---|---|
| Emulsifier: | 0.6 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray-coating has dried on, the plants are sprayed with a conidia suspension of *Pyrenophora teres*.

The plants remain in an incubation cabin at 20° C. and 100% relative atmospheric humidity for 48 hours.

The plants are placed in a greenhouse at a temperature of approximately 20° C. in a relative atmospheric humidity of approximately 80%.

Evaluation is carried out 7 days after the inoculation. 0% means an efficacy which corresponds to that of the untreated control, while an efficacy of 100% means that no infection is observed.

Active compounds, active compound concentrations and test results are shown in the table below.

TABLE C

*Pyrenophora teres* test (barley)/protective

| Active compound | Application rate of active compound in g/ha | Efficacy in % |
|---|---|---|
| According to the invention: | | |
| F₂HC–[pyrazole, N-CH₃]–C(O)–NH–[phenyl]–CH=CH–[phenyl]  (20) | 125 | 83 |

TABLE C-continued

Pyrenophora teres test (barley)/protective

| Active compound | Application rate of active compound in g/ha | Efficacy in % |
|---|---|---|
| 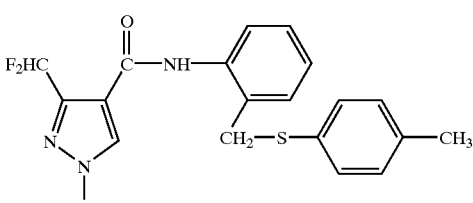 (46) | 125 | 75 |

Example D

Pseudocercosporella herpotrichoides Test; R-Strain (Wheat)/Protective

| Solvent: | 10 parts by weight of N-methyl-pyrrolidone |
|---|---|
| Emulsifier: | 0.6 parts by weight of alkylaryl polyglycol ether |

To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of active compound at stated application rates.

After the spray-coating has dried on, the plants are inoculated at the base of the stem with spores of the R-strain of Pseudocercosporella herotrichoides.

The plants are placed in a greenhouse at a temperature of approximately 10° C. and a relative atmospheric humidity of approximately 80%.

Evaluation is carried out 21 days after the inoculation. 0% means an efficacy which corresponds to that of the control, while an efficacy of 100% means that no infection is observed.

Active compounds, active compound concentrations and test results are shown in the table below.

TABLE D

Pseudocercosporella herpotrichoides test; R-strain (wheat)/protective

| Active compound | Application rate of active compound in g/ha | Efficacy in % |
|---|---|---|
| According to the invention: | | |
| 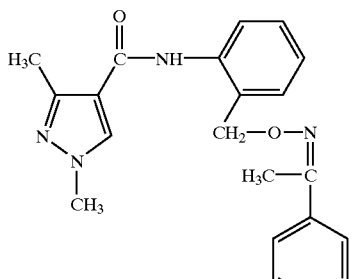 (199) | 250 | 90 |

Example E

Plutella Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are populated with caterpillars of diamond-back moth (Plutella maculipennis) while the leaves are still moist.

After the desired period of time, the kill in % is determined. 100% means that all the caterpillars have been killed; 0% means that none of the caterpillars have been killed.

Active compounds, active compound concentrations and test results are shown in the table below.

TABLE E
Plutella test
| Active compound | Active compound concentration in % | Degree of kill in % after 7 d |
|---|---|---|
| According to the invention: | | |
| 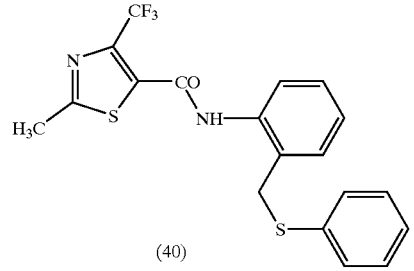 (40) | 0.1 | 100 |
| 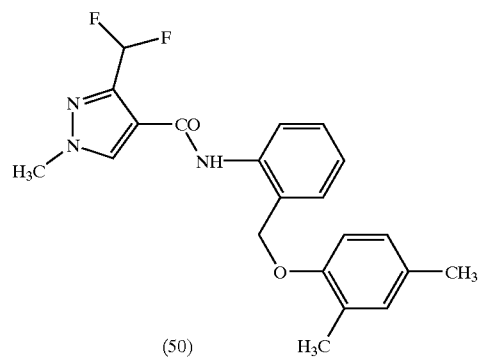 (50) | 0.1 | 100 |
| 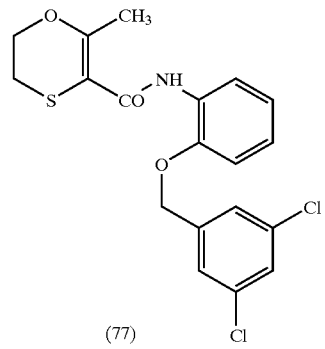 (77) | 0.1 | 100 |
| 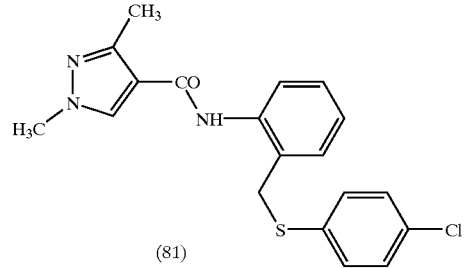 (81) | 0.1 | 100 |

TABLE E-continued

Plutella test

| Active compound | Active compound concentration in % | Degree of kill in % after 7 d |
|---|---|---|
| 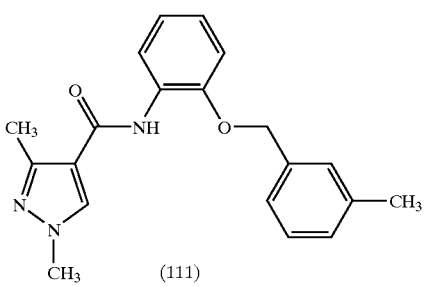 (111) | 0.1 | 100 |
| 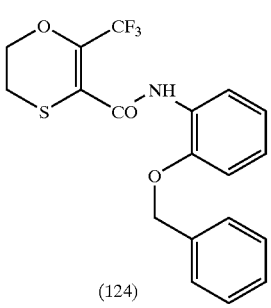 (124) | 0.1 | 90 |
| 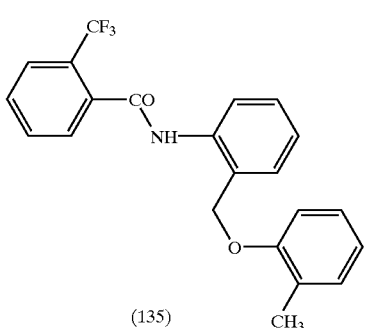 (135) | 0.1 | 100 |

Example F

Spodoptera Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the owlett moth (*Spodoptera frugiperda*) while the leaves are still moist.

After the desired period of time, the kill in % is determined. 100% means that all the caterpillars have been killed; 0% means that none of the caterpillars have been killed.

Active compounds, active compound concentrations and test results are shown in the table below.

TABLE F

Spodoptera test

| Active compound | Active compound concentration in % | Degree of kill in % after 7 d |
|---|---|---|
| According to the invention: | | |
| 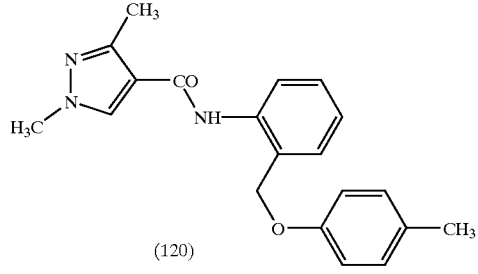 (120) | 0.1 | 100 |

Example G

Myzus Test

| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by peach aphids (*Myzus persicae*) are treated by being dipped into the preparation of active compound of the desired concentration.

After the desired period of time, the kill in % is determined. 100% means that all the aphids have been killed, 0% means that none of the aphids have been killed.

Active compounds, active compound concentrations and test results are shown in the table below.

TABLE G

Myzus Test

| Active compound | Active compound concentration in % | Degree of kill in % after 7 d |
|---|---|---|
| According to the invention: | | |
| 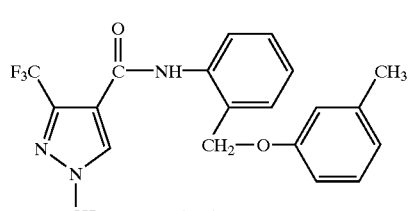 (195) | 0.1 | 95 |

Example H

Inhibitory Test with Giant Colonies of Basidiomycetes.

| Solvent: | Dimethyl sulphoxide |

To produce a suitable preparation of active compound, 0.2 parts by weight of active compound are admixed with 99.8 parts by weight of the abovementioned solvent.

An agar which has been prepared using malt extract peptone is mixed in the liquid state with the preparation of active compound at the particular desired application rate. After the agar has set, the resulting nutrient medium is incubated at 26° C. with pieces of mycelium which had been punched out of colonies of *Coniophora puteana* or *Coriolus versicolor*.

Evaluation is carried out after 3 or 7 days' storage at 26° C. by measuring the growth of the hypha and scoring the resulting inhibition in percent in comparison to the untreated control. 0% means an inhibition of growth which corresponds to that of the untreated control, while an inhibition of growth of 100% means that no growth of the hypha is observed.

Active compounds, active compound concentrations and test results are shown in the table below.

TABLE H

Inhibitory test with giant colonies of Basidiomycetes

| | Inhibition of the growth of the hypha in % with | | | | | |
|---|---|---|---|---|---|---|
| | *Coniophora puteana* at an active compound concentration of | | | *Coriolus versicolor* at an active compound concentration of | | |
| Active compound of Example No. | 1 ppm | 3 ppm | 6 ppm | 1 ppm | 3 ppm | 6 ppm |
| 5 | 70 | 80 | 100 | 70 | 90 | 100 |
| 16 | 80 | 100 | 100 | 100 | 100 | 100 |
| 18 | 70 | 100 | 100 | 70 | 100 | 100 |
| 20 | 100 | 100 | 100 | 100 | 100 | 100 |
| 39 | 70 | 80 | 90 | 90 | 100 | 100 |
| 40 | 50 | 60 | 70 | 40 | 70 | 90 |
| 45 | 70 | 80 | 90 | 90 | 100 | 100 |
| 46 | 80 | 100 | 100 | 100 | 100 | 100 |

TABLE H-continued

Inhibitory test with giant colonies of Basidiomycetes

| Active compound of Example No. | Inhibition of the growth of the hypha in % with | | | | | |
|---|---|---|---|---|---|---|
| | *Coniophora puteana* at an active compound concentration of | | | *Coriolus versicolor* at an active compound concentration of | | |
| | 1 ppm | 3 ppm | 6 ppm | 1 ppm | 3 ppm | 6 ppm |
| 50 | 100 | 100 | 100 | 100 | 100 | 100 |
| 52 | 80 | 90 | 100 | 90 | 100 | 100 |
| 78 | 70 | 80 | 90 | 90 | 90 | 100 |
| 81 | 70 | 90 | 100 | 90 | 90 | 100 |
| 84 | 80 | 80 | 100 | 90 | 100 | 100 |
| 85 | 70 | 80 | 80 | 70 | 70 | 90 |
| 119 | 100 | 100 | 100 | 100 | 100 | 100 |
| 123 | 100 | 100 | 100 | 100 | 100 | 100 |
| 139 | 100 | 100 | 100 | 100 | 100 | 100 |
| 141 | 80 | 100 | 100 | 90 | 100 | 100 |
| 142 | 70 | 90 | 100 | 90 | 90 | 100 |
| 143 | 80 | 90 | 100 | 100 | 100 | 100 |
| 144 | 70 | 90 | 100 | 90 | 100 | 100 |

Example J

Plasmopara Test (Grape Vines)/Protective

| Solvent: | 47 parts by weight of acetone |
|---|---|
| Emulsifier: | 3 parts by weight of alkyl-aryl polyglycol ether |

To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray-coating has dried on, the plants are inoculated with an aqueous spore suspension of *Plasmopara viticola* and then remain in an incubation cabin at approximately 20° C. and 100% relative atmospheric humidity for 1 day. The plants are subsequently placed in a greenhouse at approximately 21° C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, while an efficacy of 100% means that no infection is observed.

Active compounds, application rates and test results are shown in the table below.

TABLE J

Plasmopara test (grape vines)/protective

| Active compound | Application rate of active compound in g/ha | Efficacy in % |
|---|---|---|
| According to the invention: | | |
| [structure: 2-CF₃-C₆H₄-C(O)-NH-C₆H₄-CH₂-S-C₆H₄-CH₃] | 100 | 95 |
| [structure: dihydrodioxine with CH₃, S, C(O)-NH-C₆H₄-CH₂-S-C₆H₅] | 100 | 90 |

Example K

Venturia Test (Apple)/Protective

| Solution: | 47 parts by weight of acetone |
|---|---|
| Emulsifier: | 3 parts by weight of alkyl-aryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray-coating has dried on, the plants are inoculated with an aqueous Conidia suspension of the causative organism of apple scab *Venturia inaequalis* and then remain in an incubation cabin at approximately 20° C. and 100% relative atmospheric humidity for 1 day.

The plants are subsequently placed in a greenhouse at approximately 21° C. and a relative atmospheric humidity of approximately 90%.

Evaluation is carried out 12 days after the inoculation. 0% means an efficacy which corresponds to that of the control, while an efficacy of 100% means that no infection is observed.

Active compounds, application rates and test results are shown in the table below.

TABLE K

Venturia test (apple)/protective

| Active compound | Application rate of active compound in g/ha | Efficacy in % |
|---|---|---|
| According to the invention: | | |
| 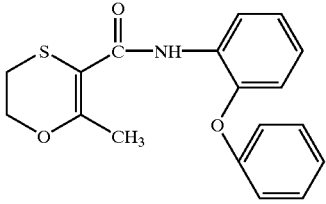 | 100 | 100 |

What is claimed is:

1. A carbanilide of the formula (I)

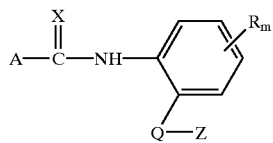

(I)

wherein

R represents halogen, nitro, alkyl having 1 to 8 carbon atoms, halogenoalkyl having 1 to 6 carbon atoms and 1 to 5 halogen atoms, alkoxy having 1 to 8 carbon atoms, halogenoalkoxy having 1 to 6 carbon atoms and 1 to 5 halogen atoms, alkylthio having 1 to 8 carbon atoms, halogenoalkylthio having 1 to 6 carbon atoms and 1 to 5 halogen atoms, alkenyloxy having 2 to 8 carbon atoms, alkynyloxy having 2 to 8 carbon atoms, cycloalkyl having 3 to 8 carbon atoms, carbalkoxy having 1 to 8 carbon atoms in the alkoxy moiety or alkoximinoalkyl having 1 to 6 carbon atoms in the alkoxy moiety and 1 to 6 carbon atoms in the alkyl moiety, m represents the numbers 0, 1, 2, 3 or 4, A represents a radical of the formula

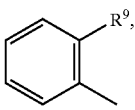

wherein $R^9$ represents trifluoromethyl,

Q represents a group of the formula

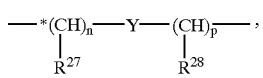

wherein $R^{27}$ and $R^{28}$ independently represent hydrogen or alkyl having 1 to 4 carbon atoms, Y represents an oxygen atom n and p independently represent the numbers 0, 1 or 2, wherein the molecular moiety labelled (*) is in each case attached to the phenyl radical of the aniline moiety, X represents oxygen and Z represents phenyl that is optionally mono- to trisubstituted with substituents selected from the group consisting of halogens, alkyl having 1 to 4 carbon atoms, alkylthio having 1 to 4 carbon atoms, halogenoalkyl having 1 or 2 carbon atoms and 1 to 5 fluorine, chlorine, and/or bromine atoms, halogenoalkoxy having 1 or 2 carbon atoms and 1 to 5 halogen atoms, alkylthio having 1 to 8 carbon atoms, halogenoalkylthio having 1 to 6 carbon atoms and 1 to 5 fluorine, chlorine, and/or bromine atoms, phenyl, and phenoxy.

2. A pesticide comprising at least one carbanilide of claim 1 and at least one of extenders and surfactants.

3. A method of controlling at least one pest comprising applying an effective amount of at least one carbanilide of claim 1 to the pest and/or its locus.

* * * * *